(12) United States Patent
Yasuhara et al.

(10) Patent No.: US 8,623,898 B2
(45) Date of Patent: Jan. 7, 2014

(54) GLYCINE TRANSPORTER INHIBITING SUBSTANCES

(75) Inventors: Akito Yasuhara, Toshima-ku (JP); Shuji Yamamoto, Toshima-ku (JP); Hiroshi Ohta, Toshima-ku (JP); Yoshihisa Shirasaki, Toshima-ku (JP); Kazunari Sakagami, Toshima-ku (JP); Masato Hayashi, Toshima-ku (JP); Tsuyoshi Shibata, Toshima-ku (JP); Youichi Shimazaki, Toshima-ku (JP); Yuko Araki, Toshima-ku (JP); Kumi Abe, Toshima-ku (JP); Xiang-Min Sun, Toshima-ku (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 178 days.

(21) Appl. No.: 13/257,258

(22) PCT Filed: Mar. 19, 2010

(86) PCT No.: PCT/JP2010/054831
§ 371 (c)(1),
(2), (4) Date: Sep. 16, 2011

(87) PCT Pub. No.: WO2010/107115
PCT Pub. Date: Sep. 23, 2010

(65) Prior Publication Data
US 2012/0010414 A1  Jan. 12, 2012

(30) Foreign Application Priority Data
Mar. 19, 2009 (JP) .................................. 2009-067945

(51) Int. Cl.
| C07D 471/04 | (2006.01) |
| C07D 405/12 | (2006.01) |
| C07D 409/12 | (2006.01) |
| C07D 405/14 | (2006.01) |
| A01N 43/64 | (2006.01) |
| A01N 43/50 | (2006.01) |
| A61K 31/41 | (2006.01) |

(52) U.S. Cl.
USPC ..... 514/383; 514/385; 548/267.6; 548/311.1; 548/315.1; 546/121; 546/272.4

(58) Field of Classification Search
USPC ................. 546/121, 272.4; 548/267.6, 311.1, 548/315.1
See application file for complete search history.

(56) References Cited

U.S. PATENT DOCUMENTS

| 7,294,644 B2 * | 11/2007 | Mayweg et al. ............... 514/399 |
| 2005/0096375 A1 | 5/2005 | McHardy et al. |
| 2006/0229455 A1 | 10/2006 | McHardy et al. |
| 2008/0300256 A1 | 12/2008 | Frank et al. |

FOREIGN PATENT DOCUMENTS

| JP | 2007-508374 A | 4/2007 |
| JP | 2008-534671 A | 8/2008 |
| JP | 2008-536829 A | 9/2008 |
| WO | 2008/065500 A2 | 6/2008 |

OTHER PUBLICATIONS

Lars et al., Current Opinion in Pharmacology, (2007), vol. 7, pp. 48-55.*
Depoortere, Ronan, et al., "Neurochemical, Electrophysiological and Pharmacological Profiles of the Selective Inhibitor of the Glycine Transporter-1 SSR504734, a Potential New Type of Antipsychotic", Neuropsychopharmacology, vol. 30, pp. 1963-1985, 2005.
Harsing, Jr., L.G., et al., "Glycine Transporter Type-1 and its Inhibitors", Current Medicinal Chemistry, vol. 13, pp. 1017-1044, 2006.
Javitt, DC, "Glutamate as a therapeutic target in psychiatric disorders", Molecular Psychiatry, vol. 9, pp. 984-997, 2004.
Lowe III, John A., et al., "An octahydro-cyclopenta[c]pyrrole series of inhibitors of the type 1 glycine transporter", Bioorganic & Medicinal Chemistry Letters, vol. 20, pp. 907-911, 2010.
Lowe III, John A., et al., "The discovery of structurally novel class of inhibitors of the type 1 glycine transporter", Bioorganic & Medicinal Chemistry Letters, vol. 19, pp. 2974-2976, 2009.
Slassi, Abdelmalik, et al., "Recent progress in the use of glycine transporter-1 inhibitors for the treatement of central and peripheral nervous system diseases", Expert Opin. Ther. Patents, vol. 14, No. 2, pp. 201-214, 2004.
International Search Report PCT/JP2010/054831, May 11, 2010.

* cited by examiner

*Primary Examiner* — Niloofar Rahmani
(74) *Attorney, Agent, or Firm* — Sughrue Mion, PLLC

(57) ABSTRACT

The present invention aims to provide novel compounds of formula [I] or pharmaceutically acceptable salts thereof that are based on a glycine uptake inhibiting action and which are useful in the prevention or treatment of such diseases as schizophrenia, Alzheimer's disease, cognitive dysfunction, dementia, anxiety disorders (generalized anxiety disorder, panic disorder, obsessive-compulsive disorder, social anxiety disorder, posttraumatic stress disorder, specific phobia, acute stress disorder, etc.), depression, drug addiction, spasm, tremor, and sleep disorder:

[Formula 1]

[I]

9 Claims, No Drawings

GLYCINE TRANSPORTER INHIBITING SUBSTANCES

CROSS REFERENCE TO RELATED APPLICATIONS

This application is a National Stage of International Application No. PCT/JP2010/054831 filed Mar. 19, 2010, claiming priority based on Japanese Patent Application No. 2009-067945 filed Mar. 19, 2009, the contents of all of which are incorporated herein by reference in their entirety.

TECHNICAL FIELD

The present invention relates to compounds having a glycine transporter inhibiting action.

BACKGROUND ART

The NMDA receptor which is one of glutamate receptors is found on the nerve cell membranes in the brain and involved in various neurophysiologic events including the plasticity of nerves, as well as cognition, attention, and memory. The NMDA receptor has a plurality of allosteric binding sites, among which is the glycine binding site (NMDA receptor complex glycine binding site). It has been reported that the NMDA receptor complex glycine binding site takes part in the activation of the NMDA receptor (Non-Patent Document 1).

An action potential arriving at the presynaptic terminal of a glycinergic nerve triggers the release of glycine into the synaptic cleft. The released glycine binds to the postsynaptic receptor or the like and is thereafter carried away by the transporter to leave the synaptic cleft. Hence, it is postulated that the glycine transporter regulates the function of the NMDA receptor through regulation of the glycine level in the extracellular fluid.

The glycine transporter (GlyT) is a protein involved in the reuptake of extracellular glycine into the cell and two subtypes, GlyT1 and GlyT2, have so far been identified. GlyT1, which mainly develops in the cerebral cortex, hippocampus, thalamus, etc., has been reported to be associated with such diseases as schizophrenia, Alzheimer's disease, cognitive dysfunction, dementia, anxiety disorders (generalized anxiety disorder, panic disorder, obsessive-compulsory disorder, social anxiety disorder, posttraumatic stress disorder, specific phobia, acute stress disorder, etc.), depression, drug addiction, spasm, tremor, and sleep disorder (Non-Patent Documents 2-4).

Compounds featuring the GlyT1 inhibiting action and having a 5-membered cyclic heteroarylamide structure have been reported in the following documents (Patent Documents 1-3 and Non-Patent Documents 5 and 6). The compounds disclosed in these Patent Documents 1-3 and Non-Patent Documents 5 and 6 are characterized by the binding of a nitrogen-containing group to the nitrogen atom in the amide structure.

CITATION LIST

Patent Documents

Patent Document 1: WO 2005/037216
Patent Document 2: WO 2006/106425
Patent Document 3: WO 2008/065500

Non-Patent Documents

Non-Patent Document 1: Molecular Psychiatry (2004) 9, 984-997
Non-Patent Document 2: Current Medicinal Chemistry, 2006, 13, 1017-1044
Non-Patent Document 3: Neuropsychopharmacology (2005), 1-23
Non-Patent Document 4: Expert Opinion on Therapeutic Patents (2004) 14 (2) 201-214
Non-Patent Document 5: Bioorganic & Medicinal Chemistry Letters (2009) 19 2974-2976
Non-Patent Document 6: Bioorganic & Medicinal Chemistry Letters (2010) 20 907-911

SUMMARY OF INVENTION

Technical Problem

The present invention aims to provide novel compounds or pharmaceutically acceptable salts thereof that are based on a glycine uptake inhibiting action and which are useful in the prevention or treatment of such diseases as schizophrenia, Alzheimer's disease, cognitive dysfunction, dementia, anxiety disorders (generalized anxiety disorder, panic disorder, obsessive-compulsory disorder, social anxiety disorder, posttraumatic stress disorder, specific phobia, acute stress disorder, etc.), depression, drug addiction, spasm, tremor, and sleep disorder.

Solution to Problem

The present inventors made intensive studies on compounds with a novel skeleton featuring an inhibitory action against GlyT1; as a result, they found that compounds represented by the following formula are superior GlyT1 inhibiting substances and this finding has eventually led to the accomplishment of the present invention.

On the following pages, the present invention is described in detail. Embodiments of the present invention (hereinafter referred to as "the invention compounds") are as set forth below.

(1) A compound of the formula [I] or a pharmaceutically acceptable salt thereof:

[Formula 1]

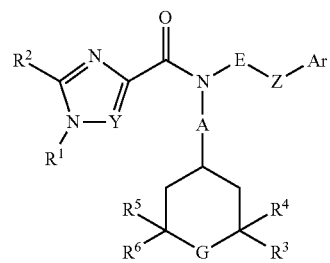

[I]

wherein $R^1$ represents a hydrogen atom, a $C_{1-6}$ alkyl group, a $C_{3-6}$ cycloalkyl group, a $C_{1-6}$ haloalkyl group, or a $C_{1-6}$ alkoxy $C_{1-6}$ alkyl group;

$R^2$ represents a hydrogen atom, a $C_{1-6}$ alkyl group, a halogen atom, or a $C_{1-6}$ alkoxy group;

or, alternatively, $R^1$ and $R^2$ may, taken together, form a $C_{3-4}$ alkylene group;

Ar represents a phenyl group or a naphthyl group, provided that the phenyl or naphthyl group may be substituted by 1 to 5 substituents selected from among a $C_{1-6}$ alkyl group, a $C_{1-6}$ alkoxy group optionally substituted by a $C_{3-6}$ cycloalkyl group, a $C_{3-6}$ cycloalkoxy group, a $C_{1-6}$ haloalkyl group, a $C_{1-6}$ haloalkoxy group, a halogen atom, a phenyl group (which phenyl group may be substituted by 1 to 5 substituents selected from among a halogen atom, a $C_{1-6}$ alkyl group, a $C_{1-6}$ hydroxyalkyl group, a $C_{1-6}$ cyanoalkyl group, a $C_{1-6}$ alkoxy group, a $C_{2-7}$ alkoxycarbonyl group, a $C_{1-6}$ haloalkyl group, a $C_{1-6}$ haloalkoxy group, and a phenoxy group), a phenoxy group that may be substituted by 1 to 5 halogen atoms, a pyridyl group, an imidazolyl group, a pyrazolyl group, and a cyano group;

Y represents a nitrogen atom or the formula CH;

Z represents a single bond or an oxygen atom;

A represents a single bond or a $C_{1-3}$ alkylene group;

E represents a $C_{1-3}$ alkylene group that may be substituted by a $C_{2-7}$ alkoxycarbonyl group, a phenyl group or a $C_{1-6}$ hydroxyalkyl group;

G represents an oxygen atom, a sulfur atom, or the formula $SO_2$;

$R^3$, $R^4$, $R^5$, and $R^6$, which may be the same or different, represent a hydrogen atom or a $C_{1-6}$ alkyl group.

(2) The compound as recited in (1) above, wherein G is an oxygen atom, or a pharmaceutically acceptable salt thereof.

(3) The compound as recited in (1) or (2) above, wherein Ar is a phenyl group substituted by 1 to 5 substituents selected from among a $C_{1-6}$ haloalkyl group, a $C_{1-6}$ haloalkoxy group, a halogen atom, a $C_{1-6}$ alkyl group, and a phenyl group (which phenyl group may be substituted by 1 to 5 substituents selected from among a halogen atom, a $C_{1-6}$ hydroxyalkyl group, a $C_{1-6}$ alkoxy group, a $C_{2-7}$ alkoxycarbonyl group, a $C_{1-6}$ haloalkyl group, a $C_{1-6}$ haloalkoxy group, a $C_{1-6}$ alkyl group, a $C_{1-6}$ cyanoalkyl group, and a phenoxy group), or a pharmaceutically acceptable salt thereof.

(4) The compound as recited in (1) above, wherein Ar is a phenyl group or a naphthyl group, provided that the phenyl or naphthyl group may be substituted by 1 to 5 substituents selected from among a $C_{1-6}$ alkyl group, a $C_{1-6}$ alkoxy group, a $C_{1-6}$ haloalkyl group, a $C_{1-6}$ haloalkoxy group, a halogen atom, a phenyl group which may be substituted by 1 to 5 halogen atoms, a phenoxy group that may be substituted by 1 to 5 halogen atoms, a pyridyl group, an imidazolyl group, a pyrazolyl group, and a cyano group; E is a $C_{1-3}$ alkylene group; G is an oxygen atom; $R^3$, $R^4$, $R^5$, and $R^6$ are each a hydrogen atom, or a pharmaceutically acceptable salt thereof.

(5) The compound as recited in any one of (1) to (4) above, wherein $R^1$ is a $C_{1-6}$ alkyl group, $R^2$ is a hydrogen atom, and Y is a nitrogen atom, or a pharmaceutically acceptable salt thereof.

(6) The compound as recited in any one of (1) to (4) above, wherein $R^1$ is a hydrogen atom or a $C_{1-6}$ alkyl group, $R^2$ is a hydrogen atom, and Y is the formula CH, or a pharmaceutically acceptable salt thereof.

(7) The compound as recited in any one of (1) to (6) above, wherein Z and A are each a single bond, and E is a methylene group, or a pharmaceutically acceptable salt thereof.

(8) The compound as recited in any one of (1) to (7) above, wherein Ar is a phenyl group substituted by 1 to 5 substituents selected from among a $C_{1-6}$ haloalkyl group, a $C_{1-6}$ haloalkoxy group, and a halogen atom, or a pharmaceutically acceptable salt thereof.

(9) A medicament comprising as an active ingredient the compound as recited in any one of (1) to (8) above or a pharmaceutically acceptable salt thereof.

(10) An agent for preventing or treating a disease selected from among schizophrenia, Alzheimer's disease, cognitive dysfunction, dementia, anxiety disorders (generalized anxiety disorder, panic disorder, obsessive-compulsory disorder, social anxiety disorder, posttraumatic stress disorder, specific phobia, acute stress disorder, etc.), depression, drug addiction, spasm, tremor, and sleep disorder, which comprises the compound as recited in any one of (1) to (8) above or a pharmaceutically acceptable salt thereof as an active ingredient.

Advantageous Effects of Invention

The invention compounds have a glycine transporter (GlyT1) inhibiting activity. The invention compounds also have high membrane permeability as shown in the Test Examples to be given later, so they are expected to excel in intestinal absorption which is an important requirement for medicaments that are to be administered orally. Further, as will be shown in the Test Examples to be given later, the invention compounds are not recognized as a substrate for the P-glycoprotein which is a discharge transporter that controls the migration of a drug into the brain, so they are also expected to provide satisfactory migration of the drug into the brain.

DESCRIPTION OF EMBODIMENTS

The term "$C_{1-6}$ alkyl group" as used herein means straight or branched alkyl groups having 1-6 carbon atoms and examples may include a methyl group, an ethyl group, a propyl group, an isopropyl group, a butyl group, an isobutyl group, a tert-butyl group, a pentyl group, an isopentyl group, and a hexyl group.

The term "$C_{3-6}$ cycloalkyl group" as used herein refers to cycloalkyl groups having 3-6 carbon atoms and they are a cyclopropyl group, a cyclobutyl group, a cyclopentyl group, and a cyclohexyl group.

The term "$C_{1-6}$ alkoxy group" as used herein means straight or branched alkoxy groups having 1-6 carbon atoms and examples may include a methoxy group, an ethoxy group, a propoxy group, an isopropoxy group, a butoxy group, an isobutoxy group, a pentyloxy group, an isopentyloxy group, and a hexyloxy group.

The term "$C_{3-6}$ cycloalkoxy group" as used herein refers to cycloalkoxy groups having 3-6 carbon atoms and they are a cyclopropoxy group, a cyclobutoxy group, a cyclopentyloxy group, and a cyclohexyloxy group.

The term "$C_{1-6}$ alkoxy $C_{1-6}$ alkyl group" as used herein refers to $C_{1-6}$ alkyl groups having a $C_{1-6}$ alkoxy group and examples may include a methoxymethyl group, a methoxyethyl group, a methoxypropyl group, a methoxybutyl group, a methoxypentyl group, a methoxyhexyl group, an ethoxymethyl group, an ethoxyethyl group, an ethoxypropyl group, an isopropoxymethyl group, an isopropoxyethyl group, an isopropoxypropyl group, a 1-methoxyethyl group, a 1-ethoxyethyl group, a 2-methoxypropyl group, and a 2-ethoxypropyl group.

The term "$C_{1-6}$ hydroxyalkyl group" as used herein refers to $C_{1-6}$ alkyl groups having a hydroxy group and examples may include a hydroxymethyl group, a hydroxyethyl group, a hydroxypropyl group, a hydroxybutyl group, a hydroxypentyl group, and a hydroxyhexyl group.

The term "$C_{1-6}$ cyanoalkyl group" as used herein refers to $C_{1-6}$ alkyl groups having a cyano group and examples may include a cyanomethyl group, a cyanoethyl group, a cyanopropyl group, a cyanobutyl group, a cyanopentyl group, and a cyanohexyl group.

The term "$C_{3-4}$ alkylene group" may be exemplified by a propane-1,3-diyl group and a butane-1,4-diyl group, and the term "$C_{1-3}$ alkylene group" may be exemplified by a methylene group, an ethylene group, an ethane-1,1-diyl group, and a propane-1,3-diyl group.

The term "halogen atom (halo)" as used herein is a fluorine atom, a chlorine atom, a bromine atom, or an iodine atom.

The term "$C_{1-6}$ haloalkyl group" as used herein means halogen-substituted straight or branched alkyl groups having 1-6 carbon atoms and the number of halogen substitutions is preferably 1 to 3, as exemplified by a fluoromethyl group, a difluoromethyl group, a trifluoromethyl group, and a trichloromethyl group.

The term "$C_{1-6}$ haloalkoxy group" as used herein means halogen-substituted straight or branched alkoxy groups having 1-6 carbon atoms and the number of halogen substitutions is a preferably 1 to 3, as exemplified by a fluoromethoxy group, a difluoromethoxy group, and a trifluoromethoxy group.

The term "$C_{2-7}$ alkoxycarbonyl group" as used herein means straight or branched alkoxycarbonyl groups having 2-7 carbon atoms and examples may include a methoxycarbonyl group, an ethoxycarbonyl group, a propoxycarbonyl group, an isopropoxycarbonyl group, a butoxycarbonyl group, an isobutoxycarbonyl group, a n-pentyloxycarbonyl group, an isopentyloxycarbonyl group, and a hexyloxycarbonyl group.

The term "pharmaceutically acceptable salt" as used herein means acid addition salts that can be accepted pharmaceutically and exemplary acids to be used may include inorganic acids such as sulfuric acid, hydrochloric acid, hydrobromic acid, nitric acid and phosphoric acid, or organic acids such as acetic acid, oxalic acid, lactic acid, citric acid, malic acid, gluconic acid, tartaric acid, fumaric acid, maleic acid, methanesulfonic acid, ethanesulfonic acid, benzenesulfonic acid, and p-toluenesulfonic acid. Conversion from the free form to the salt of interest can be realized by any conventional methods.

The following are preferred cases of the invention compounds.

Compounds wherein $R^1$ is a $C_{1-6}$ alkyl group are preferred. More preferably, the $C_{1-6}$ alkyl group is a methyl group or an ethyl group.

Compounds wherein $R^2$ is a hydrogen atom are preferred.

Compounds are preferred, wherein Ar is a phenyl group substituted by 1 to 5, more preferably 1 or 2, substituents selected from the following group A. The position of substitution by the substituents is preferably meta position and/or para position.

Group A consists of a $C_{1-6}$ haloalkyl group, a $C_{1-6}$ haloalkoxy group, a halogen atom, a $C_{1-6}$ alkyl group, and a phenyl group [which phenyl group may be substituted by 1 to 5 substituents selected from the following group B (which group B consists of a halogen atom, a $C_{1-6}$ hydroxyalkyl group, a $C_{1-6}$ alkoxy group, a $C_{2-7}$ alkoxycarbonyl group, a $C_{1-6}$ haloalkyl group, a $C_{1-6}$ haloalkoxy group, a $C_{1-6}$ alkyl group, a $C_{1-6}$ cyanoalkyl group, and a phenoxy group)].

Alternatively, Ar may be a phenyl group that is substituted by 1 or 2 substituents selected from group A consisting of a $C_{1-6}$ haloalkyl group, a $C_{1-6}$ haloalkoxy group, a halogen atom, and a phenyl group (which phenyl group may be substituted by 1 to 5 substituents selected from the above group B) and which may optionally be further substituted by a $C_{1-6}$ alkyl group.

Group A even more preferably consists of a $C_{1-6}$ haloalkyl group, a $C_{1-6}$ haloalkoxy group, and a halogen atom.

Compounds wherein Z is a single bond are preferred.

Compounds wherein A is single bond are preferred.

Compounds wherein E is a $C_{1-3}$ alkylene group that may be substituted by a $C_{2-7}$ alkoxycarbonyl group or a $C_{1-6}$ hydroxyalkyl group are preferred. More preferably, E is a $C_{1-3}$ alkylene group, and a methylene group is even more preferred.

Compounds wherein G is an oxygen atom are preferred.

Compounds wherein $R^3$, $R^4$, $R^5$, and $R^6$ are each a hydrogen atom are preferred.

The invention compounds may contain a plurality of asymmetric centers. Hence, the aforementioned compounds may occur not only in optically active forms but also in their racemic modifications; a plurality of diastereomers may also occur. All of these forms are included in the scope of the present invention. Respective isomers can be obtained by known methods, such as the use of optically active starting materials or intermediates, an optically selective reaction or a diastereoselective reaction that are carried out in the manufacture of an intermediate or an end product, or a chromatographic separation employed in the manufacture of an intermediate or an end product. If the invention compounds form hydrates or solvates, they are also included in the scope of the present invention.

The compounds according to the present invention may be administered orally or parenterally. Their administration dosage forms include tablets, capsules, granules, dispersions, powders, lozenges, ointments, creams, emulsions, suspensions, suppositories, injections, etc, all of which can be manufactured by conventional pharmaceutical formulation techniques (such as the methods specified in the 15th Revised Japanese Pharmacopoeia). These administration dosage forms may be appropriately selected depending on the symptom and age of the patient, as well as the object of treatment.

These preparations can be produced from the composition containing the compound of the present invention by incorporating in it one or more pharmacologically acceptable carriers, namely, an excipient (e.g. microcrystalline cellulose, starch, lactose, or mannitol), a binder (e.g. hydroxypropyl cellulose or polyvinylpyrrolidone), a lubricant (e.g. magnesium stearate or talc), a disintegrant (e.g. carboxymethylcellulose calcium), and various other pharmacologically acceptable additives.

The compounds according to the present invention may be administered in doses which, in the case of treating adults, range from 1 to 2000 mg per day, either once daily or in divided portions. The dose may be appropriately adjusted depending on the age, body weight and symptom of the patient.

The compounds of formula [I] can be produced by various synthesis methods. The following methods are only illustrative of the processes for producing the invention compounds and should not be taken as limiting.

In the general production processes, the "inert solvent" may be exemplified by alcohols such as methanol, ethanol, isopropanol, n-butanol, and ethylene glycol; ethers such as diethyl ether, tert-buthyl methyl ether, diisopropyl ether, tetrahydrofuran, 1,4-dioxane, and 1,2-dimethoxyethane; hydrocarbons such as pentane, hexane, heptane, toluene, benzene, and xylene; esters such as ethyl acetate and ethyl formate; ketones such as acetone and methyl ethyl ketone; halogenated carbon-based solvents such as chloroform and dichloromethane; amides such as dimethylformamide and N-methylpyrrolidone; as well as acetonitrile, dimethyl sulfoxide, water, and mixed solvents thereof.

The "base" may be exemplified by alkali metal or alkaline earth metal hydrides such as lithium hydride, sodium hydride, potassium hydride, and calcium hydride; alkali metal or alkaline earth metal amides such as lithium amide, sodium amide, lithium diisopropylamide, lithium dicyclohexylamide, lithium hexamethyldisilazide, sodium hexamethyldisilazide, and potassium hexamethyldisilazide; alkali metal or alkaline earth metal lower alkoxides such as sodium methoxide, sodium ethoxide, and potassium tert-butoxide; alkyl lithium compounds such as butyl lithium, sec-butyl lithium, tert-butyl lithium, and methyl lithium; alkali metal or alkaline earth metal hydroxides such as sodium hydroxide, potassium hydroxide, lithium hydroxide, and barium hydroxide; alkali metal or alkaline earth metal carbonates such as sodium carbonate, potassium carbonate, and cesium carbonate; alkali metal or alkaline earth metal hydrogencarbonates such as sodium hydrogencarbonate and potassium hydrogencarbonate; amines such as triethylamine, N-methylmorpholine, N,N-diisopropylethylamine, 1,8-diazabicyclo[5.4.0]undeca-7-ene (DBU), 1,5-diazabicyclo[4.3.0]non-5-ene (DBN), and N,N-dimethylaniline; as well as basic heterocyclic compounds such as pyridine, imidazole, and 2,6-lutidine. These bases may be appropriately selected depending on various reaction conditions known to skilled artisans.

The "acid" may be exemplified by inorganic acids such as hydrochloric acid, hydrobromic acid, sulfuric acid, nitric acid, and phosphoric acid; and organic acids such as p-toluenesulfonic acid, methansulfonic acid, trifluoroacetic acid, formic acid, acetic acid, citric acid, and oxalic acid. These acids may be appropriately selected depending on various reaction conditions known to skilled artisans.

The "Lewis acid" may be exemplified by boron trifluoride, aluminum trichloride, titanium tetrachloride, iron trichloride, zinc chloride, and tin tetrachloride.

General Production Process 1

[Formula 2]

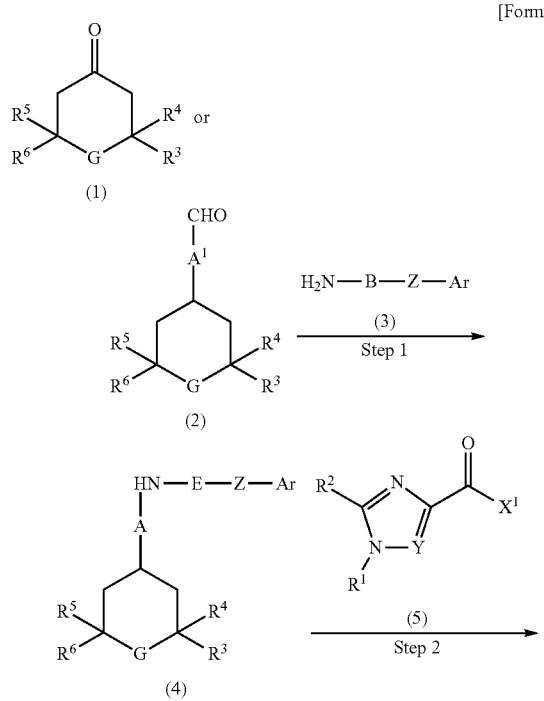

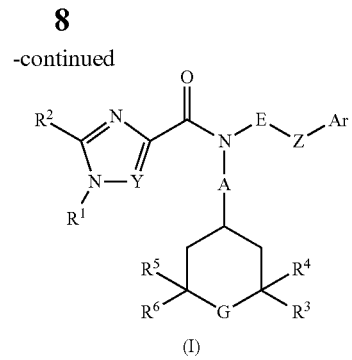

(I)

In the formula, $A^1$ represents a single bond or a $C_{1-2}$ alkylene group, $X^1$ represents a halogen atom or a hydroxyl group, and the other symbols have the same meanings as defined above. The $C_{1-2}$ alkylene group is a methylene group, an ethylene group, or an ethane-1,1-diyl group.

Step 1: Compound (1) or compound (2) and compound (3) are subjected to a reductive amination reaction in an inert solvent in the presence or absence of an acid using a reducing agent, to thereby obtain compound (4). The reducing agent here mentioned may be exemplified by sodium tri(acetoxy)borohydride, sodium cyanoborohydride, and sodium borohydride.

Step 2: Compound (4) and compound (5) where $X^1$ is a halogen atom are reacted in an inert solvent in the presence or absence of a base to obtain the invention compound (I). Alternatively, compound (4) and compound (5) where $X^1$ is a hydroxyl group are subjected to various types of amidation reaction known to skilled artisans, to thereby obtain the invention compound (I). The amidation reaction here mentioned may be exemplified by amidation reaction as performed in an inert solvent in the presence or absence of a base using a condensing agent such as O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), N,N'-dicyclohexylcarbodiimide (DCC), 1-ethyl-3-(3-dimethylaminopropyl)carbodiimide hydrochloride (EDC.HCl), diphenylphosphorylazide (DPPA), or carbonyldiimidazole (CDI), and amidation reaction via mixed acid anhydride as performed using ethyl chlorocarbonate, isobutyl chlorocarbonate or trimethylacetyl chloride. To perform the above-mentioned amidation reaction using a condensing agent, an additive such as 1-hydroxybenzotriazle (HOBt) or hydroxysuccinimide (HOSu) may also be employed depending on the need.

General Production Process 2

[Formula 3]

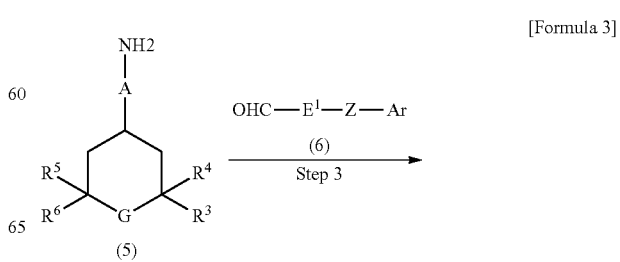

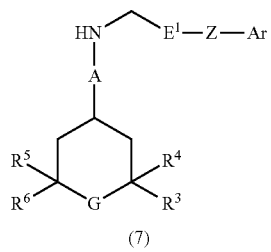

In the formula, $E^1$ represents a single bond or a $C_{1-2}$ alkylene group that may be substituted by a $C_{2-7}$ alkoxycarbonyl group, a phenyl group, or a $C_{1-6}$ hydroxyalkyl group, and the other symbols have the same meanings as defined above. Note that when $E^1$ is a single bond, Z is a single bond.

Step 3: Using compound (5) and compound (6), the method of step 1 in the general production process 1 may be employed to produce compound (7). Compound (7) is included in compound (4) obtained during the general production process 1.

General Production Process 3

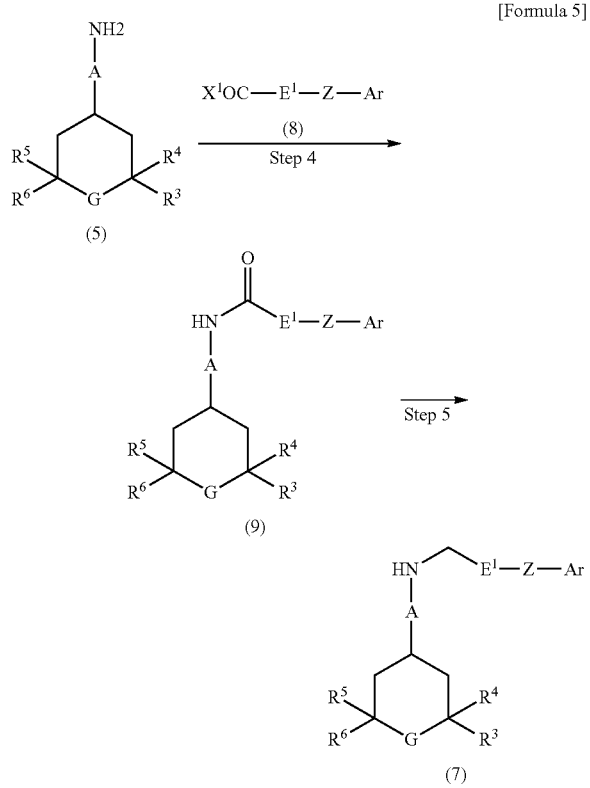

Step 4: The same technique as step 2 in the general production process 1 may be employed to produce compound (9) from compound (5) and compound (8).

Step 5: Compound (9) as amide may be converted to amine in an inert solvent using a reducing agent to produce compound (7). The reducing agent here mentioned may be exemplified by lithium aluminum hydride, diborane, or sodium borohydride (in the presence or absence of Lewis acid).

General Production Process 4

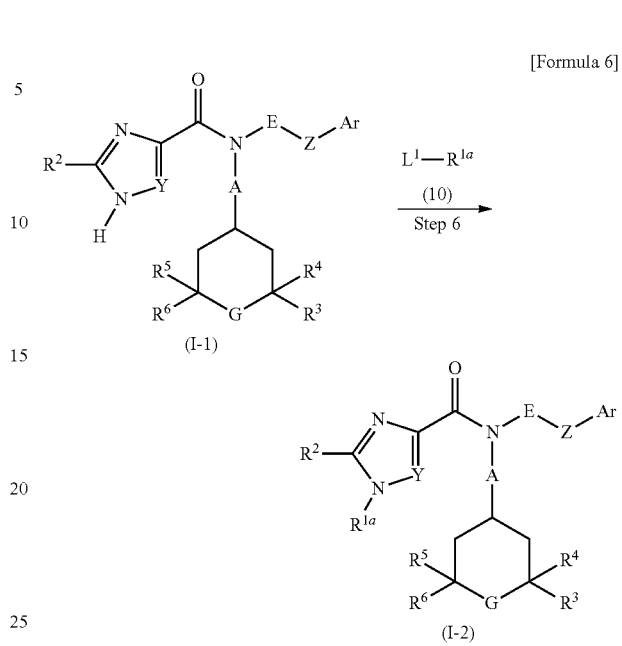

In the formula, $R^{1a}$ represents a $C_{1-6}$ alkyl group, or a $C_{1-6}$ alkoxy $C_{1-6}$ alkyl group, or a $C_{1-6}$ haloalkyl group; $L^1$ represents a leaving group such as a halogen atom, a methansulfonyloxy group, a trifluoromethanesulfonyloxy group or a p-toluenesulfonyloxy group; and the other symbols have the same meanings as defined above.

Step 6: The invention compound (I-1) where $R^1$ is a hydrogen atom and compound (10) are reacted in an inert solvent in the presence or absence of a base, to thereby obtain the invention compound (I-2).

General Production Process 5

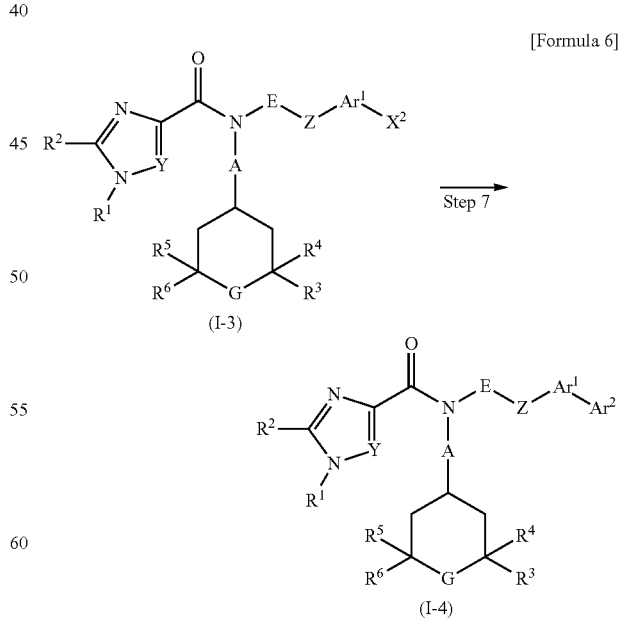

In the formula, $Ar^1$ represents a phenyl group or a naphthyl group (which phenyl or naphthyl group may be substituted by 1 to 5 substituents selected from among a $C_{1-6}$ alkyl group, a $C_{1-6}$ alkoxy group, a $C_{1-6}$ haloalkyl group, a $C_{1-6}$ haloalkoxy group, a fluorine atom, a chlorine atom, a phenoxy group that may be substituted by 1 to 5 halogen atoms, and a cyano group); $X^2$ represents a bromine atom, an iodine atom, or a trifluoromethanesulfonyloxy group; $Ar^2$ represents a phenyl group that may be substituted by 1 to 5 substituents selected from among a fluorine atom, a chlorine atom, a $C_{1-6}$ alkyl group, a $C_{1-6}$ hydroxyalkyl group, a $C_{1-6}$ cyanoalkyl group, a $C_{1-6}$ alkoxy group, a $C_{2-7}$ alkoxycarbonyl group, a $C_{1-6}$ haloalkyl group, a $C_{1-6}$ haloalkoxy group, and a phenoxy group, a pyridyl group, an imidazolyl group, or a pyrazolyl group; and the other symbols have the same meanings as defined above.

Step 7: The invention compound (I-3) may be reacted with an $Ar^2$-containing organometallic compound in an inert solvent in the presence or absence of a base using a palladium catalyst, optionally together with a ligand for the palladium catalyst, to thereby obtain the invention compound (I-4).

The palladium catalyst here mentioned may be exemplified by palladium acetate, tris(dibenzylideneacetone)dipalladium, tetraquistriphenylphosphine palladium, (1,3-diisopropylimidazol-2-ylidene) (3-chloropyridyl)palladium(II) dichloride, [1,3-bis(2,6-diisopropylphenyl)imidazol-2-ylidene] (3-chloropyridyl)palladium(II) dichloride, and chloro[1,1'-bis(diphenylphosphino)ferrocene]palladium; the ligand may be exemplified by triphenylphosphine, 2,2-bis(diphenylphosphino)-1,1-binaphthyl (BINAP), 2-(di-tert-butylphosphino)biphenyl, and 9,9-dimethyl-4,5-bis(diphenylphosphino)xanthene (Xantphos); the $Ar^2$-containing organometallic compound may be exemplified by a Grignard reagent such as $Ar^2MgCl$, a zinc reagent such as $Ar^2ZnCl$, a boron reagent having $Ar^2$ bound to boric acid or borate, and a tin reagent such as $Ar^2SnBu_3$.

General Production Process 6

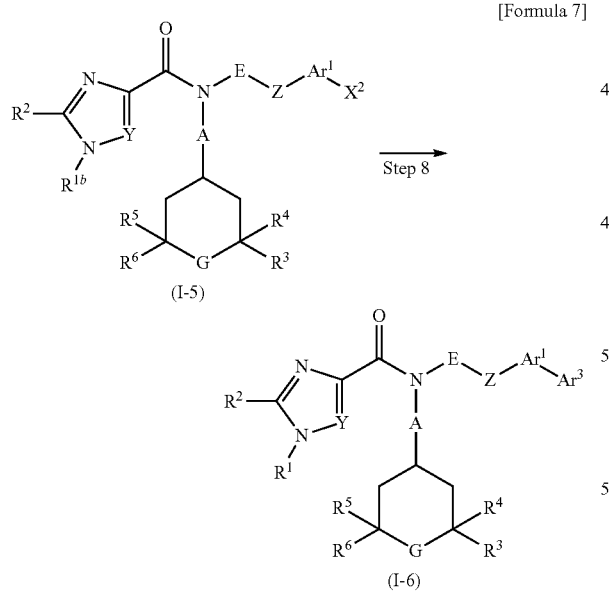

[Formula 7]

In the formula, $R^{1b}$ represents a $C_{1-6}$ alkyl group, a $C_{3-6}$ cycloalkyl group, a $C_{1-6}$ haloalkyl group, or a $C_{1-6}$ alkoxy $C_{1-6}$ group; $Ar^3$ represents a 1H-imidazol-1-yl group or a 1H-pyrazol-1-yl group; and the other symbols have the same meanings as defined above.

Step 8: The invention compound (I-5) where $R^1$ is not a hydrogen atom may be reacted with imidazole or pyrazole in the presence of a copper catalyst and an amine ligand in an inert solvent in the presence or absence of a base, to thereby obtain the invention compound (I-6).

The copper catalyst here mentioned may be exemplified by copper(I) oxide, copper(I) iodide, copper(I) bromide, and copper(I) acetate; the amine ligand may be exemplified by N,N-dimethylethylenediamine, 1,2-cyclohexanediamine, and phenanthroline.

General Production Process 7

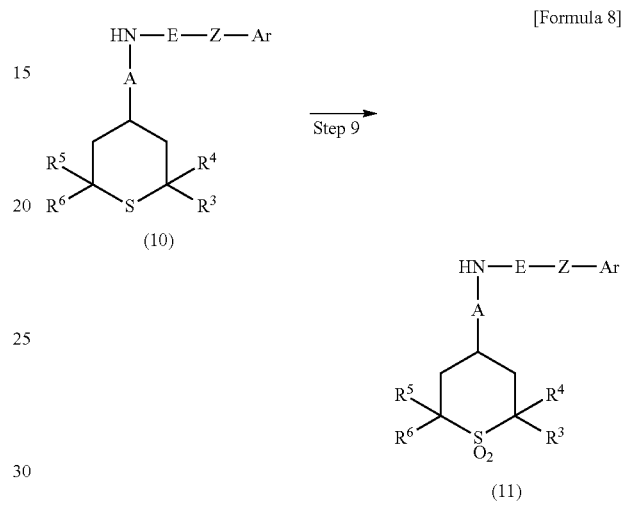

[Formula 8]

Step 9: Compound (10) as sulfide may be converted to sulfone by oxidation in an inert solvent using an oxidizing agent to produce compound (11). The oxidizing agent here mentioned may be exemplified by sodium periodate, peracetic acid, 3-chloroperbenzoic acid, hydrogen peroxide, Oxone, ozone, potassium permanganate, and sodium hypochlorite.

General Production Process 8

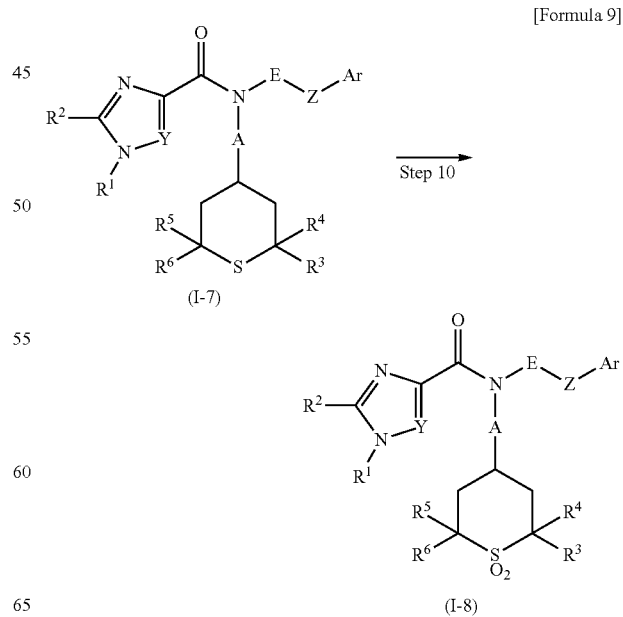

[Formula 9]

Step 10: The same technique as step 9 in the general production process 7 may be employed to obtain the invention compound (I-8) from the invention compound (I-7).

On the following pages, the present invention will be described in greater detail by means of production examples, working examples, and test examples but it should be understood that those examples are by no means intended to limit the present invention.

In the case of purification by column chromatography, Biotage (registered trademark) SNAPCartridge KP-NH was used as the NH silica gel cartridge, and Biotage (registered trademark) SNAPCartridge KP-Sil was used as the silica gel cartridge. In the case of purification by TLC, Silica gel 60F254 (Merck) was used as the TLC (silica gel), and TLC plate NH (Fuji Silysia) was used as the TLC (NH silica gel plate).

The microwave reactor mentioned in the production examples and working examples was of the following model.
Microwave Reactor: Initiator (Biotage AB)

The instrument data set forth in the production examples and working examples were obtained by measurement with the following instruments.

MS spectra: Shimadzu LCMS-2010EV or micromass Platform LC

NMR spectra: [$^1$H-NMR] 600 MHz: JNM-ECA 600 (JEOL, Ltd.); 500 MHz: JNM-ECA 500 (JEOL, Ltd.); 300 MHz: UNITYNOVA 300 (Varian Inc.); 200 MHz: GEMINI 2000/200 (Varian Inc.)

The compound names given in the working examples were assigned by ACD/Name (ACD/Labs 11.01, Advanced Chemistry Development Inc.)

The following abbreviations were used in production examples, working examples, and test examples.
TLC: thin-layer chromatography
DIAD: diisopropylazodicarboxylate
ALX5407: N-[(3R)-3-([1,1'-biphenyl]-4-yloxy)-3-(4-fluorophenyl)propyl]-N-methylglycine HCl salt

PRODUCTION EXAMPLE 1

N-[3-(Trifluoromethoxy)benzyl]tetrahydro-2H-pyran-4-amine

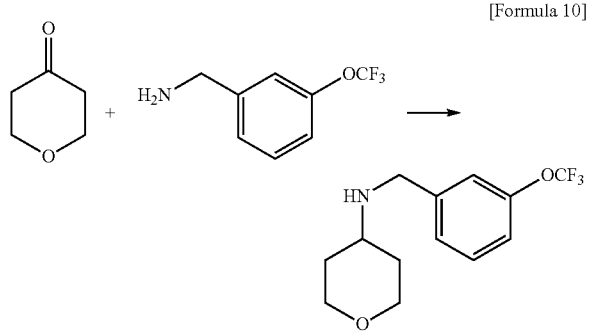

[Formula 10]

To a solution of 4-oxo-1H-pyran (200 mg) in chloroform (2 mL), 3-trifluoromethoxybenzylamine (380 mg) was added and the resulting mixture was stirred at room temperature for 30 minutes. Sodium (triacetoxy)borohydride (850 mg) was added and the resulting mixture was stirred for an hour. To the reaction mixture, an aqueous solution of 6 M sodium hydroxide was added and extraction was conducted with ethyl acetate. The solvents were distilled off under reduced pressure and the resulting residue was purified by column chromatography (NH silica gel cartridge; hexane/ethyl acetate=9:1 to 1:9) to give the titled compound (450 mg).

1H NMR (600 MHz, CHLOROFORM-d) d ppm 1.40-1.49 (m, 2 H) 1.82-1.89 (m, 2 H) 2.66-2.76 (m, 1 H) 3.36-3.44 (m, 2 H) 3.85 (s, 2 H) 3.94-4.02 (m, 2 H) 7.08-7.38 (m, 4 H)

(ESI pos.) m/z: 275 ([M+H]$^+$)

By similar procedures, the following compounds were synthesized.

2-(Tetrahydro-2H-pyran-4-yl)-N-[3-(trifluoromethoxy)benzyl]ethaneamine

1H NMR (200 MHz, CHLOROFORM-d) d ppm 1.16-1.71 (m, 7 H) 2.58-2.73 (m, 2 H) 3.37 (td, J=11.76, 1.98 Hz, 2 H) 3.77-4.01 (m, 5 H) 7.02-7.42 (m, 4 H)

(ESI pos.) m/z: 304 ([M+H]$^+$)

1-(Tetrahydro-2H-pyran-4-yl)-N-[3-(trifluoromethoxy)benzyl]methaneamine

1H NMR (600 MHz, CHLOROFORM-d) d ppm 1.22-1.33 (m, 2 H) 1.59-1.73 (m, 3 H) 2.45-2.52 (m, 2 H) 3.32-3.39 (m, 2 H) 3.78 (s, 2 H) 3.90-3.98 (m, 2 H) 7.03-7.35 (m, 4 H)

(ESI pos.) m/z: 290 ([M+H]$^+$)

N-(3-Chlorobenzyl)tetrahydro-2H-pyran-4-amine

1H NMR (200 MHz, CHLOROFORM-d) d ppm 1.31-1.56 (m, 2 H) 1.78-1.95 (m, 2 H) 2.61-2.81 (m, 1 H) 3.30-3.48 (m, 2 H) 3.81 (s, 2 H) 3.91-4.07 (m, 2 H) 7.18-7.40 (m, 4 H)

(ESI pos.) m/z: 226 ([M+H]$^+$)

N-[3-(Trifluoromethyl)benzyl]tetrahydro-2H-pyran-4-amine

1H NMR (200 MHz, CHLOROFORM-d) d ppm 1.22-1.58 (m, 2 H) 1.78-1.96 (m, 2 H) 2.62-2.83 (m, 1 H) 3.31-3.50 (m, 2 H) 3.84-4.07 (m, 4 H) 7.35-7.65 (m, 4 H)

(ESI pos.) m/z: 260 ([M+H]$^+$)

N-[2-(Trifluoromethoxy)benzyl]tetrahydro-2H-pyran-4-amine

1H NMR (600 MHz, CHLOROFORM-d) d ppm 1.40-1.49 (m, 2 H) 1.82-1.89 (m, 2 H) 2.65-2.75 (m, 1 H) 3.34-3.43 (m, 2 H) 3.88 (s, 2 H) 3.93-4.02 (m, 2 H) 7.20-7.32 (m, 3 H) 7.44-7.50 (m, 1 H)

(ESI pos.) m/z: 276 ([M+H]$^+$)

N-(2-Phenoxyethyl)tetrahydro-2H-pyran-4-amine

1H NMR (600 MHz, CHLOROFORM-d) d ppm 1.40-1.50 (m, 2 H) 1.82-1.91 (m, 2 H) 2.72-2.79 (m, 1 H) 3.00-3.07 (m, 2 H) 3.37-3.46 (m, 2 H) 3.97-4.02 (m, 2 H) 4.06-4.11 (m, 2 H) 6.88-6.98 (m, 3 H) 7.25-7.31 (m, 2 H)

(ESI pos.) m/z: 222 ([M+H]$^+$)

N-(3-Methoxybenzyl)tetrahydro-2H-pyran-4-amine

1H NMR (200 MHz, CHLOROFORM-d) d ppm 1.32-1.57 (m, 2 H) 1.76-1.96 (m, 2 H) 2.61-2.83 (m, 1 H) 3.29-3.51 (m, 2 H) 3.76-3.88 (m, 5 H) 3.90-4.06 (m, 2 H) 6.74-6.97 (m, 3 H) 7.17-7.31 (m, 1 H)

(ESI pos.) m/z: 222 ([M+H]$^+$)

N-(3-Chloro-4-fluorobenzyl)tetrahydro-2H-pyran-4-amine

1H NMR (200 MHz, CHLOROFORM-d) d ppm 1.32-1.55 (m, 2 H) 1.75-1.94 (m, 2 H) 2.60-2.80 (m, 1 H) 3.31-3.48 (m, 2 H) 3.78 (s, 2 H) 3.90-4.06 (m, 2 H) 7.01-7.24 (m, 2 H) 7.34-7.44 (m, 1 H)
(ESI pos.) m/z: 244 ([M+H]$^+$)

N-[4-fluoro-3-(trifluoromethyl)benzyl]tetrahydro-2H-pyran-4-amine

1 NMR (200 MHz, CHLOROFORM-d) d ppm 1.31-1.56 (m, 2 H) 1.77-1.95 (m, 2 H) 3.30-3.49 (m, 2 H) 3.84 (s, 2 H) 3.91-4.07 (m, 2 H) 7.07-7.22 (m, 1 H) 7.44-7.64 (m, 2 H)
(ESI pos.) m/z: 278 ([M+H]$^+$)

2-(Tetrahydro-2H-pyran-4-ylamino)ethanol

1H NMR (600 MHz, CHLOROFORM-d) d ppm 1.34-1.45 (m, 2 H) 1.82-1.88 (m, 2 H) 2.64-2.72 (m, 1 H) 2.78-2.85 (m, 2 H) 3.37-3.44 (m, 2 H) 3.61-3.68 (m, 2 H) 3.94-4.02 (m, 2 H)
(ESI pos.) m/z: 146 ([M+H]$^+$)

N-[2-(2-Chlorophenyl)ethyl]tetrahydro-2H-pyran-4-amine

1H NMR (600 MHz, CHLOROFORM-d) d ppm 1.34-1.44 (m, 2 H) 1.78-1.87 (m, 2 H) 2.68-2.76 (m, 1 H) 2.87-2.97 (m, 4 H) 3.35-3.45 (m, 2 H) 3.92-4.02 (m, 2 H) 7.13-7.36 (m, 4 H)
(ESI pos.) m/z: 240 ([M+H]$^+$)

N-(4-Iodobenzyl)tetrahydro-2H-pyran-4-amine

1H NMR (600 MHz, CHLOROFORM-d) d ppm 1.37-1.47 (m, 2 H) 1.79-1.88 (m, 2 H) 2.63-2.73 (m, 1 H) 3.32-3.42 (m, 2 H) 3.76 (s, 2 H) 3.92-4.00 (m, 2 H) 7.08 (d, J=8.25 Hz, 2 H) 7.64 (d, J=8.25 Hz, 2 H) (ESI pos.) m/z: 318 ([M+H]$^+$)

N-[3-Fluoro-5-(trifluoromethyl)benzyl]tetrahydro-2H-pyran-4-amine

1H NMR (600 MHz, CHLOROFORM-d) d ppm 1.39-1.49 (m, 2 H) 1.82-1.90 (m, 2 H) 2.67-2.75 (m, 1 H) 3.35-3.43 (m, 2 H) 3.89 (s, 2 H) 3.94-4.02 (m, 2 H) 7.16-7.33 (m, 2 H) 7.41 (s, 1 H)
(ESI pos.) m/z: 278 ([M+H]$^+$)

N-Benzyltetrahydro-2H-pyran-4-amine

1H NMR (600 MHz, CHLOROFORM-d) d ppm 1.40-1.49 (m, 2 H) 1.81-1.89 (m, 2 H) 2.69-2.77 (m, 1 H) 3.34-3.43 (m, 2 H) 3.82 (s, 2 H) 3.93-4.00 (m, 2 H) 7.21-7.35 (m, 5 H)
(ESI pos.) m/z: 192 ([M+H]$^+$)

N-(Biphenyl-4-ylmethyl)tetrahydro-2H-pyran-4-amine

1H NMR (600 MHz, CHLOROFORM-d) d ppm 1.43-1.51 (m, 2 H) 1.86-1.92 (m, 2 H) 2.73-2.80 (m, 1 H) 3.37-3.43 (m, 2 H) 3.87 (s, 2 H) 3.96-4.02 (m, 2 H) 7.31-7.47 (m, 5 H) 7.54-7.60 (m, 4 H)
(ESI pos.) m/z: 268 ([M+H]$^+$)

N-[4-Fluoro-3-(trifluoromethoxy)benzyl]tetrahydro-2H-pyran-4-amine

1H NMR (600 MHz, CHLOROFORM-d) d ppm 1.38-1.48 (m, 2 H) 1.81-1.88 (m, 2 H) 2.65-2.74 (m, 1 H) 3.35-3.43 (m, 2 H) 3.81 (s, 2 H) 3.93-4.02 (m, 2 H) 7.09-7.35 (m, 3 H)
(ESI pos.) m/z: 294 ([M+H]$^+$)

N-(3,5-Dichlorobenzyl)tetrahydro-2H-pyran-4-amine

1H NMR (600 MHz, CHLOROFORM-d) d ppm 1.37-1.47 (m, 2 H) 1.81-1.88 (m, 2 H) 2.65-2.73 (m, 1 H) 3.35-3.44 (m, 2 H) 3.79 (s, 2 H) 3.93-4.01 (m, 2 H) 7.24 (s, 3 H)
(ESI pos.) m/z: 260 ([M+H]$^+$)

N-[4-(Trifluoromethoxy)benzyl]tetrahydro-2H-pyran-4-amine

1H NMR (600 MHz, CHLOROFORM-d) d ppm 1.37-1.48 (m, 2 H) 1.81-1.89 (m, 2 H) 2.67-2.75 (m, 1 H) 3.34-3.43 (m, 2 H) 3.82 (s, 2 H) 3.94-4.00 (m, 2 H) 7.16 (d, J=8.00 Hz, 2 H) 7.35 (d, J=8.00 Hz, 2 H)
(ESI pos.) m/z: 276 ([M+H]+)

N-(3-Iodobenzyl)tetrahydro-2H-pyran-4-amine

1H NMR (600 MHz, CHLOROFORM-d) d ppm 1.38-1.48 (m, 2 H) 1.80-1.87 (m, 2 H) 2.66-2.74 (m, 1 H) 3.34-3.41 (m, 2 H) 3.76 (s, 2 H) 3.93-4.00 (m, 2 H) 7.05 (t, J=8.25 Hz, 1 H) 7.28 (d, J=8.25 Hz, 1 H) 7.57 (d, J=8.25 Hz, 1 H) 7.69 (s, 1 H)
(ESI pos.) m/z: 318 ([M+H]+)

N-(3,4-Dichlorobenzyl)tetrahydro-2H-pyran-4-amine

1H NMR (600 MHz, CHLOROFORM-d) d ppm 1.36-1.47 (m, 2 H) 1.80-1.87 (m, 2 H) 2.65-2.72 (m, 1 H) 3.34-3.41 (m, 2 H) 3.78 (s, 2 H) 3.93-4.00 (m, 2 H) 7.13-7.19 (m, 1 H) 7.33-7.46 (m, 2 H)
(ESI pos.) m/z: 260 ([M+H]+)

N-[3-Bromo-4-fluorobenzyl]tetrahydro-2H-pyran-4-amine

1H NMR (200 MHz, CHLOROFORM-d) d ppm 1.37-1.56 (m, 2 H) 1.77-1.93 (m, 2 H) 2.61-2.79 (m, 1 H) 3.31-3.48 (m, 2 H) 3.78 (s, 2 H) 3.91-4.06 (m, 2 H) 6.99-7.59 (m, 3 H)
(ESI pos.) m/z: 288 ([M+H]+)

N-[2-Fluoro-5-(trifluoromethoxy)benzyl]tetrahydro-2H-pyran-4-amine

1H NMR (200 MHz, CHLOROFORM-d) d ppm 1.37-1.51 (m, 2 H) 1.78-1.95 (m, 2 H) 2.45-2.81 (m, 3 H) 3.29-3.49 (m, 2 H) 3.85-4.05 (m, 4 H) 6.98-7.35 (m, 3 H)
(ESI pos.) m/z: 294 ([M+H]$^+$)

N-[3-(Difluoromethoxy)benzyl]tetrahydro-2H-pyran-4-amine

1H NMR (200 MHz, CHLOROFORM-d) d ppm 1.38-1.51 (m, 2 H) 1.76-1.95 (m, 2 H) 2.44-2.81 (m, 3 H) 3.29-3.49 (m, 2 H) 3.84 (s, 2 H) 3.90-4.05 (m, 2 H) 6.11-6.91 (m, 1 H) 6.94-7.39 (m, 4 H)
(ESI pos.) m/z: 258 ([M+H]$^+$)

N-[1-(3-Chlorophenyl)ethyl]tetrahydro-2H-pyran-4-amine

1H NMR (600 MHz, CHLOROFORM-d) d ppm 1.27-1.41 (m, 5 H) 1.60-1.67 (m, 1 H) 1.84-1.91 (m, 1 H) 2.44-2.52 (m, 1 H) 3.23-3.33 (m, 2 H) 3.86-3.98 (m, 3 H) 7.15-7.34 (m, 4 H)
(ESI pos.) m/z: 240 ([M+H]+)

N-[2-[3-(Trifluoromethoxy)phenyl]ethyl]tetrahydro-2H-pyran-4-amine

1H NMR (600 MHz, CHLOROFORM-d) d ppm 1.32-1.42 (m, 2 H) 1.75-1.84 (m, 2 H) 2.63-2.96 (m, 5 H) 3.32-3.44 (m, 2 H) 3.90-4.02 (m, 2 H) 7.02-7.17 (m, 3 H) 7.27-7.35 (m, 1 H)
(ESI pos.) m/z: 290 ([M+H]+)

Methyl N-(tetrahydro-2H-pyran-4-yl)-3-(trifluoromethoxy)phenyl alaninate

1H NMR (600 MHz, CHLOROFORM-d) d ppm 1.23-1.47 (m, 2 H) 1.64-1.73 (m, 2 H) 2.55-2.64 (m, 1 H) 2.88-2.97 (m, 2 H) 3.27-3.39 (m, 2 H) 3.57-3.68 (m, 4 H) 3.83-3.94 (m, 2 H) 7.05-7.15 (m, 3 H) 7.28-7.33 (m, 1 H)

N-(Diphenylmethyl)tetrahydro-2H-pyran-4-amine

1H NMR (600 MHz, CHLOROFORM-d) d ppm 1.38-1.44 (m, 2 H) 1.84-1.94 (m, 2 H) 2.59-2.67 (m, 1 H) 3.25-3.36 (m, 2 H) 3.87-3.99 (m, 2 H) 5.04 (s, 1 H) 7.18-7.23 (m, 2 H) 7.27-7.32 (m, 4 H) 7.34-7.43 (m, 4 H)
(ESI pos.) m/z: 268 ([M+H]+)

N-(3-Bromo-4-fluorobenzyl)-2,2-dimethyltetrahydro-2H-pyran-4-amine

1H NMR (600 MHz, CHLOROFORM-d) d ppm 1.19 (s, 3 H) 1.25 (s, 3 H) 1.25-1.34 (m, 2 H) 1.77-1.87 (m, 2 H) 2.81-2.88 (m, 1 H) 3.60-3.67 (m, 1 H) 3.73-3.82 (m, 3 H) 7.04-7.08 (m, 1 H) 7.21-7.25 (m, 1 H) 7.53-7.56 (m, 1 H)
(ESI pos.) m/z: 316, 318 ([M+H]+)

N-(3-Bromo-4-fluorobenzyl)-2,6-dimethyltetrahydro-2H-pyran-4-amine

1H NMR (600 MHz, CHLOROFORM-d) d ppm 1.15 (d, J=6.42 Hz, 4 H) 1.37-1.61 (m, 4 H) 3.04-3.07 (m, 1 H) 3.73 (s, 2 H) 3.87-3.94 (m, 2 H) 7.04-7.08 (m, 1 H) 7.21-7.26 (m, 1 H) 7.51-7.58 (m, 1 H)
(ESI pos.) m/z: 316, 318 ([M+H]+)

N-[3-(Cyclopropylmethoxy)-4-fluorobenzyl]tetrahydro-2H-pyran-4-amine

1H NMR (600 MHz, CHLOROFORM-d) d ppm 0.31-0.37 (m, 2 H) 0.59-0.68 (m, 2 H) 1.19-1.49 (m, 4 H) 1.80-1.88 (m, 2 H) 2.67-2.76 (m, 1 H) 3.34-3.42 (m, 2 H) 3.75-3.83 (m, 4 H) 3.91-4.01 (m, 2 H) 6.73-7.25 (m, 3 H)
(ESI pos.) m/z: 262 ([M+H]+)

N-[3-(Cyclopentyloxy)-4-fluorobenzyl]tetrahydro-2H-pyran-4-amine

1H NMR (600 MHz, CHLOROFORM-d) d ppm 1.40-1.48 (m, 2 H) 1.57-1.66 (m, 2 H) 1.75-1.95 (m, 8 H) 2.69-2.76 (m, 1 H) 3.35-3.42 (m, 2 H) 3.79 (s, 2 H) 3.94-4.00 (m, 2 H) 4.74-4.79 (m, 1 H) 6.72-7.23 (m, 4 H)
(ESI pos.) m/z: 276 ([M+H]+)

N-[4-Fluoro-3-(3-methylbutoxy)benzyl]tetrahydro-2H-pyran-4-amine

1H NMR (600 MHz, CHLOROFORM-d) d ppm 0.96 (d, J=6.88 Hz, 6 H) 1.40-1.49 (m, 2 H) 1.64-1.70 (m, 2 H) 1.79-1.88 (m, 3 H) 2.69-2.76 (m, 1 H) 3.34-3.42 (m, 2 H) 3.80 (s, 2 H) 3.93-4.02 (m, 4 H) 6.76-7.25 (m, 4 H)
(ESI pos.) m/z: 278 ([M+H]+)

N-(3-Bromo-4-fluorobenzyl)tetrahydro-2H-pyran-4-amine

1H NMR (200 MHz, CHLOROFORM-d) d ppm 1.32-1.55 (m, 2 H) 1.77-1.92 (m, 2 H) 2.59-2.79 (m, 1 H) 3.31-3.47 (m, 2 H) 3.78 (s, 2 H) 3.91-4.05 (m, 2 H) 7.00-7.58 (m, 3 H)

PRODUCTION EXAMPLE 2

N-(2-Hydroxyethyl)-1-methyl-N-(tetrahydro-2H-pyran-4-yl)-1H-imidazole-4-carboxamide

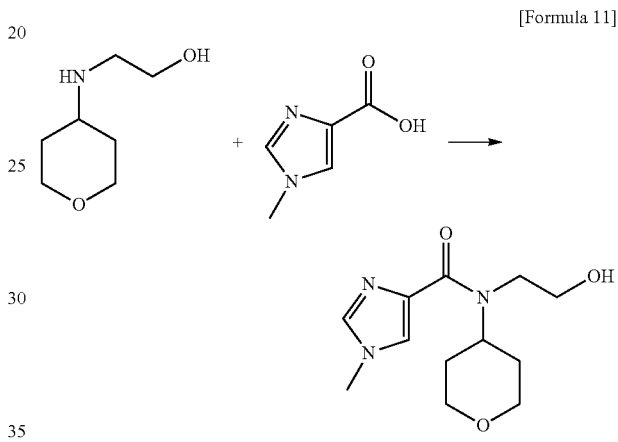

[Formula 11]

A mixture of 2-(tetrahydro-2H-pyran-4-ylamino)ethanol (3.45 g), 1-methyl-1H-imidazole-4-carboxylic acid (3.00 g), HATU (13.6 g), diisopropylethylamine (12.4 mL) and acetonitrile (52 mL) was stirred at room temperature for 2 hours. The solvents were distilled off under reduced pressure and the resulting residue was purified by column chromatography (silica gel cartridge; chloroform/methanol=98:2 to 96:4) to give the titled compound (2.34 g).

1H NMR (600 MHz, CHLOROFORM-d) d ppm 1.76-2.01 (m, 4 H) 3.38-4.10 (m, 11 H) 4.48-5.43 (m, 1 H) 7.35 (s, 1 H) 7.39 (s, 1 H)
(ESI pos.) m/z: 254 ([M+H]$^+$)

By similar procedures, the following compounds were synthesized.

N-(Tetrahydro-2H-pyran-4-yl)-N-[3-(trifluoromethyl)benzyl]-1H-1,2,4-triazole-3-carboxamide 1H NMR (600 MHz, CHLOROFORM-d) d ppm 1.55-1.90 (m, 4 H) 3.35-3.56 (m, 2 H) 3.88-4.04 (m, 2 H) 4.59-5.95 (m, 3 H) 7.33-8.15 (m, 5 H)
(ESI pos.) m/z: 355 ([M+H]$^+$)
(ESI neg.) m/z: 353 ([M−H]−)

N-[2-(2-Chlorophenyl)ethyl]-N-(tetrahydro-2H-pyran-4-yl)-1H-1,2,4-triazole-3-carboxamide 1H NMR (600 MHz, CHLOROFORM-d) d ppm 1.68-2.18 (m, 4 H) 3.10-5.77 (m, 9 H) 7.15-8.23 (m, 5 H)
(ESI pos.) m/z: 335 ([M+H]$^+$)

N-(Naphthalen-2-ylmethyl)-N-(tetrahydro-2H-pyran-4-yl)-1H-1,2,4-triazole-3-carboxamide 1H NMR (600 MHz, DMSO-d$_6$) d ppm 1.52-1.90 (m, 4 H) 3.03-3.29 (m, 2 H) 3.73-5.47 (m, 5 H) 7.38-8.77 (m, 8 H)
(ESI neg.) m/z: 335 ([M−H]−)

N-(3-Iodobenzyl)-N-(tetrahydro-2H-pyran-4-yl)-1H-1,2,4-triazole-3-carboxamide

1H NMR (600 MHz, CHLOROFORM-d) d ppm 1.58-1.91 (m, 4 H) 3.40-3.55 (m, 2 H) 3.93-4.05 (m, 2 H) 4.74 (s, 3 H) 7.01-7.07 (m, 1 H) 7.16-7.26 (m, 1 H) 7.53-7.66 (m, 2 H) 7.98-8.26 (m, 1 H)
(ESI pos.) m/z: 413 ([M+H]$^+$)
(ESI neg.) m/z: 411 ([M−H]−)

N-(4-Fluoro-3-methoxybenzyl)-N-(tetrahydro-2H-pyran-4-yl)-1H-1,2,4-triazole-3-carboxamide 1H NMR (600 MHz, CHLOROFORM-d) d ppm 1.58-1.94 (m, 4 H) 3.39-3.53 (m, 2 H) 3.80-4.05 (m, 5 H) 4.57-5.70 (m, 3 H) 6.69-7.05 (m, 3 H) 8.00-8.18 (m, 1 H)
(ESI pos.) m/z: 335 ([M+H]$^+$)
(ESI neg.) m/z: 333 ([M−H]−)

N-(3,4-Dichlorobenzyl)-N-(tetrahydro-2H-pyran-4-yl)-1H-1,2,4-triazole-3-carboxamide 1H NMR (600 MHz, CHLOROFORM-d) d ppm 1.60-1.89 (m, 4 H) 3.41-3.54 (m, 2 H) 3.94-4.05 (m, 2 H) 4.72 (s, 3 H) 7.04-7.17 (m, 1 H) 7.28-7.43 (m, 2 H) 7.93-8.25 (m, 1 H)
(ESI pos.) m/z: 355 ([M+H]$^+$)

N-(3,4-Difluorobenzyl)-N-(tetrahydro-2H-pyran-4-yl)-1H-1,2,4-triazole-3-carboxamide 1H NMR (600 MHz, CHLOROFORM-d) d ppm 1.59-1.90 (m, 4 H) 3.39-3.53 (m, 2 H) 3.94-4.04 (m, 2 H) 4.73 (s, 3 H) 6.94-7.16 (m, 3 H) 8.00-8.29 (m, 1 H)
(ESI pos.) m/z: 323 ([M+H]$^+$)
(ESI neg.) m/z: 321 ([M−H]−)

N-(3-Bromo-4-fluorobenzyl)-N-(tetrahydro-2H-pyran-4-yl)-1H-1,2,4-triazole-3-carboxamide 1H NMR (200 MHz, CHLOROFORM-d) d ppm 1.52-2.00 (m, 4 H) 3.34-3.56 (m, 2 H) 3.90-4.09 (m, 2 H) 4.57-5.77 (m, 3 H) 6.98-7.25 (m, 2 H) 7.35-7.56 (m, 1 H) 7.99-8.31 (m, 1 H)
(ESI pos.) m/z: 383 ([M+H]+)
(ESI neg.) m/z: 381 ([M−H]−)

N-(3-Phenoxybenzyl)-N-(tetrahydro-2H-pyran-4-yl)-1H-1,2,4-triazole-3-carboxamide 1H NMR (600 MHz, CHLOROFORM-d) d ppm 1.57-1.91 (m, 4 H) 3.39-3.56 (m, 2 H) 3.89-4.05 (m, 2 H) 4.60-5.97 (m, 3 H) 6.81-7.35 (m, 10 H) 7.92-8.25 (m, 1 H)
(ESI pos.) m/z: 379 ([M+H]$^+$)
(ESI neg.) m/z: 377 ([M−H]−)

N-[2-Fluoro-5-(trifluoromethoxy)benzyl]-N-(tetrahydro-2H-pyran-4-yl)-1H-1,2,4-triazole-3-carboxamide 1H NMR (600 MHz, CHLOROFORM-d) d ppm 1.58-1.92 (m, 4 H) 3.42-3.56 (m, 2 H) 3.93-4.06 (m, 2 H) 4.67-5.78 (m, 3 H) 7.03-7.16 (m, 3 H) 7.98-8.22 (m, 1 H)
(ESI pos.) m/z: 389 ([M+H]$^+$)
(ESI neg.) m/z: 387 ([M−H]−)

N-(3-Methylbenzyl)-N-(tetrahydro-2H-pyran-4-yl)-1H-1,2,4-triazole-3-carboxamide

1H NMR (600 MHz, CHLOROFORM-d) d ppm 1.58-1.94 (m, 4 H) 2.24-2.37 (m, 3 H) 3.38-3.54 (m, 2 H) 3.91-4.04 (m, 2 H) 4.61-5.83 (m, 3 H) 6.93-7.23 (m, 4 H) 7.97-8.24 (m, 1 H)
(ESI pos.) m/z: 301 ([M+H]$^+$)
(ESI neg.) m/z: 299 ([M−H]−)

N-(3-Cyanobenzyl)-N-(tetrahydro-2H-pyran-4-yl)-1H-1,2,4-triazole-3-carboxamide

1H NMR (600 MHz, CHLOROFORM-d) d ppm 1.56-1.91 (m, 4 H) 3.41-3.56 (m, 2 H) 3.94-4.06 (m, 2 H) 4.67-5.89 (m, 3 H) 7.37-7.64 (m, 4 H) 7.92-8.26 (m, 1 H)
(ESI pos.) m/z: 312 ([M+H]$^+$)
(ESI neg.) m/z: 310 ([M−H]−)

N-[3-(Pyridin-2-yl)benzyl]-N-(tetrahydro-2H-pyran-4-yl)-1H-1,2,4-triazole-3-carboxamide 1H NMR (600 MHz, CHLOROFORM-d) d ppm 1.62-1.94 (m, 4 H) 3.37-3.53 (m, 2 H) 3.90-4.03 (m, 2 H) 4.60-5.84 (m, 3 H) 7.19-8.16 (m, 8 H) 8.64-8.74 (m, 1 H)
(ESI pos.) m/z: 364 ([M+H]$^+$)
(ESI neg.) m/z: 362 ([M−H]−)

N-[3-(Difluoromethoxy)benzyl]-N-(tetrahydro-2H-pyran-4-yl)-1H-1,2,4-triazole-3-carboxamide 1H NMR (600 MHz, CHLOROFORM-d) d ppm 1.60-1.93 (m, 4 H) 3.40-3.56 (m, 2 H) 3.94-4.06 (m, 2 H) 4.78 (s, 3 H) 6.31-6.60 (m, 1 H) 6.97-7.17 (m, 3 H) 7.27-7.34 (m, 1 H) 7.93-8.21 (m, 1 H)
(ESI pos.) m/z: 353 ([M+H]$^+$)
(ESI neg.) m/z: 351 ([M−H]−)

N-[1-(3-Chlorophenyl)ethyl]-N-(tetrahydro-2H-pyran-4-yl)-1H-1,2,4-triazole-3-carboxamide (ESI pos.) m/z: 335 ([M+H]+)

N-[3,4-Bis(difluoromethoxy)benzyl]-N-(tetrahydro-2H-pyran-4-yl)-1H-1,2,4-triazole-3-carboxamide 1H NMR (600 MHz, CHLOROFORM-d) d ppm 1.37-1.87 (m, 4 H) 3.38-3.48 (m, 2 H) 3.88-4.02 (m, 2 H) 4.57-5.57 (m, 3 H) 6.28-6.64 (m, 2 H) 7.03-7.19 (m, 3 H) 8.02-8.25 (m, 1 H)
(ESI pos.) m/z: 419 ([M+H]+)
(ESI neg.) m/z: 417 ([M−H]−)

N-[4-Chloro-3-(trifluoromethoxy)benzyl]-N-(tetrahydro-2H-pyran-4-yl)-1H-1,2,4-triazole-3-carboxamide 1H NMR (600 MHz, CHLOROFORM-d) d ppm 1.56-1.91 (m, 4 H) 3.33-3.54 (m, 2 H) 3.92-4.04 (m, 2 H) 4.74 (s, 3 H) 7.10-7.46 (m, 3 H) 7.99-8.34 (m, 1 H)
(ESI pos.) m/z: 405 ([M+H]+)
(ESI neg.) m/z: 403 ([M−H]−)

N-[3-Chloro-5-(trifluoromethoxy)benzyl]-N-(tetrahydro-2H-pyran-4-yl)-1H-1,2,4-triazole-3-carboxamide 1H NMR (600 MHz, CHLOROFORM-d) d ppm 1.70-1.97 (m, 4 H) 3.40-3.55 (m, 2 H) 3.92-4.05 (m, 2 H) 4.61-5.69 (m, 3 H) 6.92-7.31 (m, 3 H) 8.04-8.32 (m, 1 H)
(ESI pos.) m/z: 405 ([M+H]+)
(ESI neg.) m/z: 403 ([M−H]−)

N-(Tetrahydro-2H-pyran-4-yl)-N-[4-(trifluoromethoxy)benzyl]-1H-1,2,4-triazole-3-carboxamide 1H NMR (600 MHz, CHLOROFORM-d) d ppm 1.65-1.94 (m, 4 H) 3.36-3.57 (m, 2 H) 3.90-4.06 (m, 2H) 4.58-5.89 (m, 3 H) 7.08-8.77 (m, 5 H)
(ESI pos.) m/z: 371 ([M+H]+)
(ESI neg.) m/z: 369 ([M−H]−)

N-[3-(Cyclopropylmethoxy)-4-fluorobenzyl]-N-(tetrahydro-2H-pyran-4-yl)-1H-1,2,4-triazole-3-carboxamide 1H NMR (600 MHz, CHLOROFORM-d) d ppm 0.27-0.38 (m, 2 H) 0.56-0.69 (m, 2 H) 1.17-1.34 (m, 1 H) 1.59-1.99 (m, 4 H) 3.40-3.56 (m, 2 H) 3.70-3.81 (m, 2 H) 3.92-4.04 (m, 2 H) 4.57-5.97 (m, 3 H) 6.66-6.93 (m, 3 H) 7.12-7.24 (m, 1 H) 7.90-8.28 (m, 1 H)
(ESI pos.) m/z: 357 ([M+H]+)
(ESI neg.) m/z: 355 ([M−H]−)

N-[3-(Cyclopentyloxy)-4-fluorobenzyl]-N-(tetrahydro-2H-pyran-4-yl)-1H-1,2,4-triazole-3-carboxamide 1H NMR (600 MHz, CHLOROFORM-d) d ppm 1.51-1.99 (m, 12 H) 3.39-3.53 (m, 2 H) 3.92-4.03 (m, 2 H) 4.59-5.84 (m, 4 H) 6.67-6.87 (m, 3 H) 7.14-7.22 (m, 1 H) 7.99-8.23 (m, 1 H)
(ESI pos.) m/z: 371 ([M+H]+)
(ESI neg.) m/z: 369 ([M−H]−)

N-[4-Fluoro-3-(3-methylbutoxy)benzyl]-N-(tetrahydro-2H-pyran-4-yl)-1H-1,2,4-triazole-3-carboxamide 1H NMR (600 MHz, CHLOROFORM-d) d ppm 0.89-0.99 (m, 6 H) 1.48-2.01 (m, 7 H) 3.38-3.57 (m, 2 H) 3.86-4.05 (m, 4 H) 4.57-5.88 (m, 3 H) 6.69-6.88 (m, 3 H) 7.12-7.25 (m, 1 H) 7.95-8.23 (m, 1 H)
(ESI pos.) m/z: 373 ([M+H]+)

PRODUCTION EXAMPLE 3

N-(Tetrahydro-2H-pyran-4-yl)-N-[3-(trifluoromethoxy)benzyl]imidazo[1,2-a]pyridine-2-carboxamide

[Formula 12]

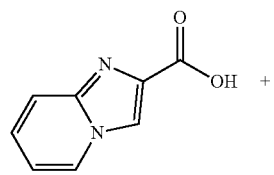

+

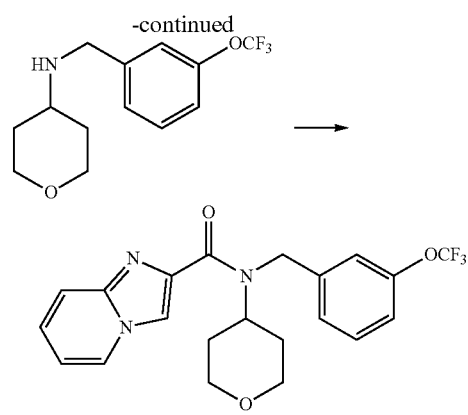

N-[3-(Trifluoromethoxy)benzyl]tetrahydro-2H-pyran-4-amine (242 mg), imidazo[1,2-a]pyridine-2-carboxylic acid (194 mg), EDC.HCl (199 mg), HOBt (138 mg), dimethylformamide (5 mL) and triethylamine (0.33 mL) was stirred overnight at room temperature. The solvents were distilled off under reduced pressure and following extraction with ethyl acetate, the extract was washed with a saturated aqueous solution of sodium hydrogencarbonate and saturated saline, and dried over anhydrous magnesium sulfate. The desiccant was filtered off and, thereafter, the solvents were concentrated. The residue was purified by column chromatography (NH silica gel cartridge; ethyl acetate) to give the titled compound (286 mg).

1H NMR (600 MHz, CHLOROFORM-d) d ppm 1.58-1.97 (m, 4 H) 3.35-3.58 (m, 2 H) 3.92-4.04 (m, 2 H) 4.70-5.75 (m, 3 H) 6.75-7.66 (m, 7 H) 8.00-8.24 (m, 2 H)
(ESI pos.) m/z: 420 ([M+H]+)

By similar procedures, the following compounds were synthesized.

N-(Tetrahydro-2H-pyran-4-ylmethyl)-N-[3-(trifluoromethoxy)benzyl]-1H-1,2,4-triazole-3-carboxamide 1H NMR (600 MHz, CHLOROFORM-d) d ppm 1.31-1.66 (m, 4 H) 1.92-2.14 (m, 1 H) 3.24-3.47 (m, 4 H) 3.90-4.16 (m, 4 H) 4.80-5.52 (m, 2 H) 7.09-7.41 (m, 4 H) 8.18-8.33 (m, 1 H)
(ESI pos.) m/z: 385 ([M+H]+)
(ESI neg.) m/z: 383 ([M−H]−)

N-(3,5-Dichlorobenzyl)-N-(tetrahydro-2H-pyran-4-yl)-1H-1,2,4-triazole-3-carboxamide 1H NMR (600 MHz, CHLOROFORM-d) d ppm 1.58-1.91 (m, 4 H) 3.40-3.58 (m, 2 H) 3.93-4.08 (m, 2 H) 4.64-5.81 (m, 3 H) 7.02-7.30 (m, 3 H) 7.96-8.27 (m, 1 H)
(ESI neg.) m/z: 354 ([M−H]−)

PRODUCTION EXAMPLE 4

N-(Naphthalen-2-ylmethyl)tetrahydro-2H-pyran-4-amine

[Formula 13]

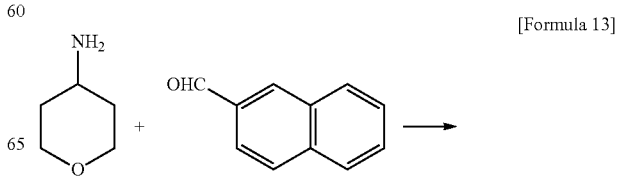

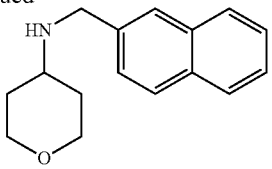

To a solution of tetrahydro-2H-pyran-4-amine (500 mg) in chloroform (5 mL), 2-naphthoaldehyde (772 mg) was added and the resulting mixture was stirred for 30 minutes. Sodium (triacetoxy)borohydride (1.57 g) was added and the resulting mixture was stirred for 4 hours at room temperature. To the reaction mixture, an aqueous solution of 1 M sodium hydroxide was added and after stirring the resulting mixture, the chloroform layer was separated and dried over anhydrous sodium sulfate. After filtering off the desiccant, the solvent was distilled off under reduced pressure and the resulting residue was purified by column chromatography (silica gel cartridge; chloroform/methanol=100:0 to 97:3) to give the titled compound (821 mg).

1H NMR (600 MHz, CHLOROFORM-d) d ppm 1.44-1.53 (m, 2 H) 1.86-1.92 (m, 2 H) 2.73-2.81 (m, 1 H) 3.35-3.42 (m, 2 H) 3.95-4.02 (m, 4 H) 7.43-7.49 (m, 3 H) 7.74-7.77 (m, 1 H) 7.78-7.85 (m, 3 H)

(ESI pos.) m/z: 242 ([M+H]$^+$)

By similar procedures, the following compounds were synthesized.

N-(4-Fluoro-3-methoxybenzyl)tetrahydro-2H-pyran-4-amine

1H NMR (200 MHz, CHLOROFORM-d) d ppm 1.37-1.50 (m, 2 H) 1.77-1.95 (m, 2 H) 2.62-2.82 (m, 1 H) 3.29-3.49 (m, 2 H) 3.79 (s, 2 H) 3.87-4.06 (m, 5 H) 6.75-7.09 (m, 3 H)

(ESI pos.) m/z: 240 ([M+H]$^+$)

N-(3,4-Difluorobenzyl)tetrahydro-2H-pyran-4-amine

1H NMR (600 MHz, CHLOROFORM-d) d ppm 1.38-1.47 (m, 2 H) 1.80-1.87 (m, 2 H) 2.65-2.73 (m, 1 H) 3.35-3.42 (m, 2 H) 3.78 (s, 2 H) 3.93-4.01 (m, 2 H) 7.00-7.21 (m, 3 H)

(ESI pos.) m/z: 228 ([M+H]$^+$)

N-(3-Phenoxybenzyl)tetrahydro-2H-pyran-4-amine

1H NMR (600 MHz, CHLOROFORM-d) d ppm 1.37-1.48 (m, 2 H) 1.77-1.88 (m, 2 H) 2.66-2.76 (m, 1 H) 3.33-3.44 (m, 2 H) 3.81 (s, 2 H) 3.91-4.01 (m, 2 H) 6.84-7.39 (m, 9 H)

(ESI pos.) m/z: 284 ([M+H]$^+$)

N-[3-(Trifluoromethoxy)benzyl]tetrahydro-2H-pyran-4-amine

1H NMR (600 MHz, CHLOROFORM-d) d ppm 1.41-1.51 (m, 2 H) 1.81-1.91 (m, 2 H) 2.35 (s, 3 H) 2.69-2.78 (m, 1 H) 3.35-3.44 (m, 2 H) 3.79 (s, 2 H) 3.93-4.01 (m, 2 H) 7.02-7.25 (m, 4 H)

(ESI pos.) m/z: 206 ([M+H]$^+$)

3-[(Tetrahydro-2H-pyran-4-ylamino)methyl]benzonitrile

1H NMR (600 MHz, CHLOROFORM-d) d ppm 1.39-1.49 (m, 2 H) 1.80-1.91 (m, 2 H) 2.64-2.77 (m, 1 H) 3.34-3.46 (m, 2 H) 3.87 (s, 2 H) 3.93-4.03 (m, 2 H) 7.37-7.71 (m, 4 H)

(ESI pos.) m/z: 217 ([M+H]$^+$)

N-[3-(Pyridin-2-yl)benzyl]tetrahydro-2H-pyran-4-amine

1H NMR (600 MHz, CHLOROFORM-d) d ppm 1.43-1.52 (m, 2 H) 1.85-1.92 (m, 2 H) 2.74-2.81 (m, 1 H) 3.36-3.43 (m, 2 H) 3.92 (s, 2 H) 3.95-4.02 (m, 2 H) 7.21-7.26 (m, 1 H) 7.38-7.47 (m, 2 H) 7.72-7.88 (m, 3 H) 7.98 (s, 1 H) 8.68-8.72 (m, 1 H)

(ESI pos.) m/z: 269 ([M+H]$^+$)

N-[3,4-Bis(difluoromethoxy)benzyl]tetrahydro-2H-pyran-4-amine

1H NMR (600 MHz, CHLOROFORM-d) d ppm 1.36-1.88 (m, 4 H) 2.65-2.74 (m, 1 H) 3.33-3.42 (m, 2 H) 3.81 (s, 2 H) 3.93-4.00 (m, 2 H) 6.35-6.66 (m, 2 H) 7.15-7.28 (m, 3 H)

(ESI pos.) m/z: 324 ([M+H]+)

N-[4-Chloro-3-(trifluoromethoxy)benzyl]tetrahydro-2H-pyran-4-amine

1H NMR (600 MHz, CHLOROFORM-d) d ppm 1.37-1.87 (m, 4 H) 2.64-2.72 (m, 1 H) 3.34-3.41 (m, 2 H) 3.82 (s, 2 H) 3.93-4.01 (m, 2 H) 7.19-7.24 (m, 1 H) 7.31-7.42 (m, 2 H)

(ESI pos.) m/z: 310 ([M+H]+)

N-[3-Chloro-5-(trifluoromethoxy)benzyl]tetrahydro-2H-pyran-4-amine

1H NMR (600 MHz, CHLOROFORM-d) d ppm 1.35-1.48 (m, 2 H) 1.77-1.88 (m, 2 H) 2.60-2.74 (m, 1 H) 3.30-3.42 (m, 2 H) 3.82 (s, 2 H) 3.90-4.01 (m, 2 H) 7.04-7.33 (m, 3 H)

(ESI pos.) m/z: 310 ([M+H]+)

PRODUCTION EXAMPLE 5

N-(3-Bromo-4-fluorobenzyl)tetrahydro-2H-thiopyran-4-amine

[Formula 14]

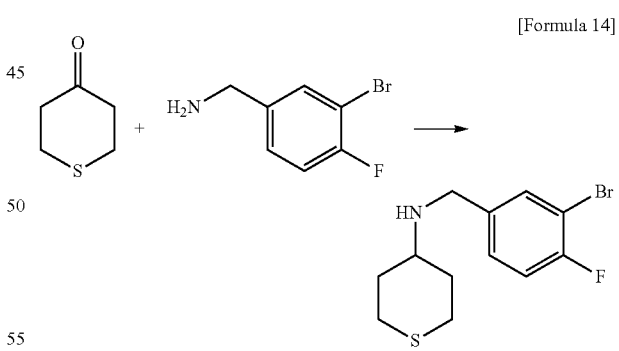

To a solution of tetrahydro-4H-thiopyran-4-one (1.16 g) in chloroform (50 mL), 3-bromo-4-fluorobenzylamine (2.41 g) was added and the resulting mixture was stirred at room temperature for an hour. Sodium (triacetoxy)borohyride (6.36 g) was added and the resulting mixture was stirred overnight. To the reaction mixture, an aqueous solution of 2 M sodium hydroxide was added and after stirring the resulting mixture, extraction was performed with chloroform. The chloroform layer was dried over anhydrous sodium sulfate. After filtering off the desiccant, the solvent was distilled off under reduced pressure and the resulting residue was purified by column chromatography (silica gel cartridge; chloroform/methanol=100:0 to 99:1) to give the titled compound (1.72 g).

1H NMR (200 MHz, CHLOROFORM-d) d ppm 1.46-1.66 (m, 2 H) 2.10-2.29 (m, 2 H) 2.42-2.85 (m, 5 H) 3.77 (s, 2 H) 6.99-7.26 (m, 2 H) 7.49-7.59 (m, 1 H)

By similar procedures, the following compounds were synthesized.

N-[3-(Trifluoromethyl)benzyl]tetrahydro-2H-thiopyran-4-amine

1H NMR (200 MHz, CHLOROFORM-d) d ppm 1.48-1.69 (m, 2 H) 2.13-2.29 (m, 2 H) 2.43-2.81 (m, 5 H) 3.88 (s, 2 H) 7.37-7.64 (m, 4 H)

(ESI pos.) m/z: 276 ([M+H]+)

N-[3-Methyl-5-(trifluoromethoxy)benzyl]tetrahydro-2H-thiopyran-4-amine

1H NMR (200 MHz, CHLOROFORM-d) d ppm 1.47-1.69 (m, 2 H) 2.11-2.28 (m, 2 H) 2.36 (s, 3 H) 2.39-2.80 (m, 5 H) 3.79 (s, 2 H) 6.88-7.11 (m, 3 H)

(ESI pos.) m/z: 306 ([M+H]+)

PRODUCTION EXAMPLE 6

N-(3-Bromo-4-fluorobenzyl)-1-methyl-N-(tetrahydro-2H-thiopyran-4-yl)-1H-imidazole-4-carboxamide

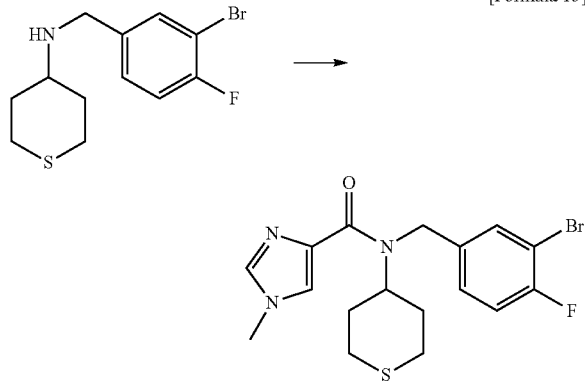

[Formula 15]

A mixture of N-(3-bromo-4-fluorobenzyl)tetrahydro-2H-thiopyran-4-amine (1.72 g), 1-methyl-1H-imidazole-4-carboxylic acid (0.71 g), EDC.HCl (1.63 g), HOBt (0.87 g), dimethylformamide (30 mL) and triethylamine (1.8 mL) was stirred overnight at room temperature. The solvent was distilled off under reduced pressure and after extraction with ethyl acetate, the extract was washed with a saturated aqueous solution of sodium hydrogencarbonate and saturated saline, and dried over anhydrous magnesium sulfate. After filtering off the desiccant, the solvent was concentrated. The residue was purified by column chromatography (NH silica gel cartridge; ethyl acetate) to give the titled compound (1.55 g).

1H NMR (200 MHz, CHLOROFORM-d) d ppm 1.65-2.27 (m, 4 H) 2.51-2.93 (m, 4 H) 3.64-3.81 (m, 3 H) 4.41-5.55 (m, 3 H) 6.93-7.62 (m, 5 H)

The 3-cyclopropylimidazole-3-carboxylic acid used as the starting material in the production of the invention compounds was prepared from ethyl 3-cyclopropylimidazole-3-carboxylate which had been obtained from 3-N,N-(dimethylamino)-2-isocyanoacrylic acid and cyclopropylamine by the method described in Org. Lett., (2002) 4133; to be more specific, an aqueous solution of 6 M sodium hydroxide (0.74 mL) was added to a mixture of the ethyl 3-cyclopropylimidazole-3-carboxylate (400 mg), tetrahydrofuran (2 mL) and water (0.5 mL) and the resulting mixture was stirred at room temperature for 2 days to effect hydrolysis; the product was concentrated under reduced pressure and used as the starting material without further treatment.

Ethyl 3-cyclopropylimidazole-3-carboxylate

1H NMR (200 MHz, CHLOROFORM-d) d ppm 0.95-1.11 (m, 4 H) 1.38 (t, J=7.03 Hz, 3 H) 3.32-3.46 (m, 1 H) 4.36 (q, J=7.03 Hz, 2 H) 7.57 (s, 1 H) 7.65 (s, 1 H) (ESI pos.) m/z: 181 ([M+H]+)

EXAMPLE 1

1-Methyl-N-(tetrahydro-2H-pyran-4-yl)-N-[3-(trifluoromethoxy)benzyl]-1H-imidazole-4-carboxamide

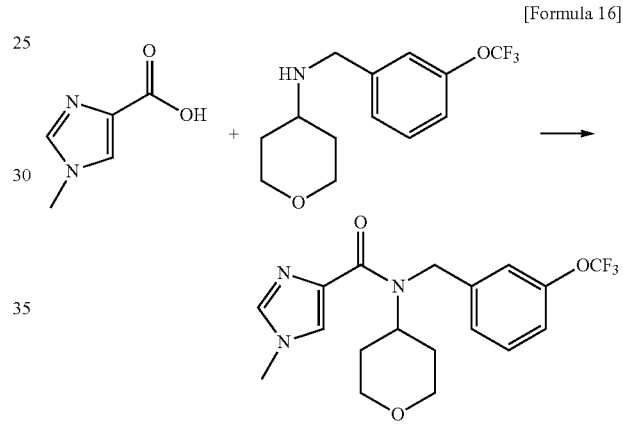

[Formula 16]

A mixture of N-[3-(trifluoromethoxy)benzyl]tetrahydro-2H-pyran-4-amine (450 mg), 1-methyl-1H-imidazole-4-carboxylic acid (210 mg), EDC.HCl (320 mg), HOBt (250 mg) and acetonitrile (5 mL) was stirred at room temperature for an hour. Acetonitrile was distilled off under reduced pressure and an aqueous solution of 6 M sodium hydroxide was added. Extraction was conducted with ethyl acetate and the solvent was concentrated. The residue was purified by column chromatography (NH silica gel cartridge; ethyl acetate) to give the titled compound (90 mg).

EXAMPLE 2

2-Bromo-1-methyl-N-(tetrahydro-2H-pyran-4-yl)-N-[3-(trifluoromethoxy)benzyl]-1H-imidazole-4-carboxamide

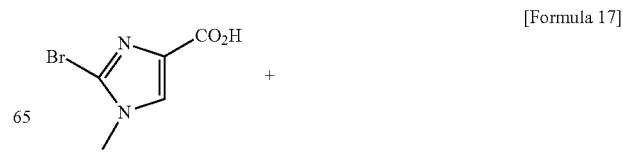

[Formula 17]

-continued

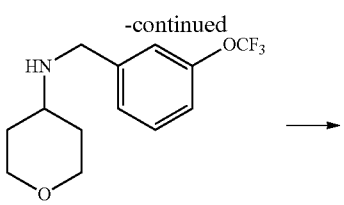

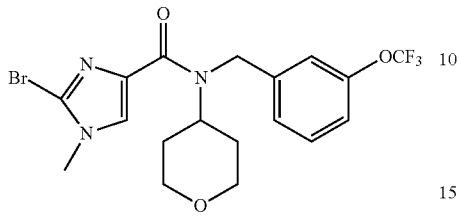

A mixture of N-[3-(trifluoromethoxy)benzyl]tetrahydro-2H-pyran-4-amine (190 mg), 2-bromo-1-methyl-1H-imidazole-4-carboxylic acid (100 mg), HATU, diisopropylethylamine (190 mg) and acetonitrile (3 mL) was stirred overnight at room temperature. Acetonitrile was distilled off under reduced pressure and the residue was purified by column chromatography (NH silica gel cartridge; hexane/ethyl acetate=3:1 to 1:2) to give the titled compound (130 mg).

EXAMPLE 3

1-Methyl-N-(tetrahydro-2H-pyran-4-yl)-N-[3-(trifluoromethoxy)benzyl]-1H-1,2,4-triazole-3-carboxamide

[Formula 18]

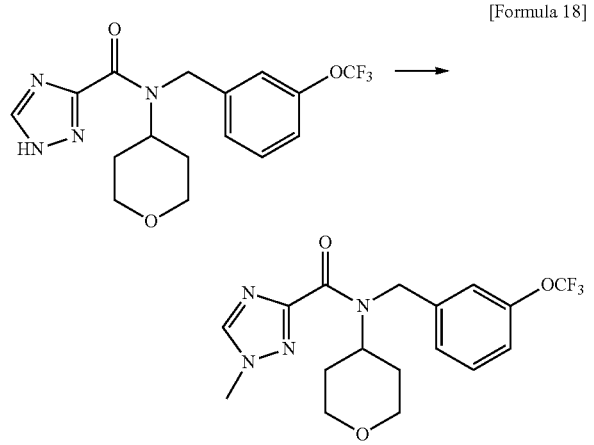

To a solution of N-(tetrahydro-2H-pyran-4-yl)-N-[3-(trifluoromethoxy)benzyl]-1H-1,2,4-triazole-3-carboxamide (138 mg) in DMF (2 mL), sodium hydride (60%, 18 mg) was added and the resulting mixture was stirred for 10 minutes; thereafter, methyl iodide (35 µL) was added and the resulting mixture was stirred overnight at room temperature. To the reaction mixture, a saturated aqueous solution of sodium hydrogencarbonate was added and extraction was conducted with ethyl acetate. The ethyl acetate layer was washed with saturated saline and dried over anhydrous magnesium sulfate. After filtering off the desiccant, the filtrate was concentrated under reduced pressure and the resulting residue was purified by column chromatography (NH silica gel cartridge; hexane/ethyl acetate=1:0 to 1:3) to give the titled compound (75 mg).

EXAMPLE 4

2-Methoxy-1-methyl-N-(tetrahydro-2H-pyran-4-yl)-N-[3-(trifluoromethoxy)benzyl]-1H-imidazole-4-carboxamide

[Formula 19]

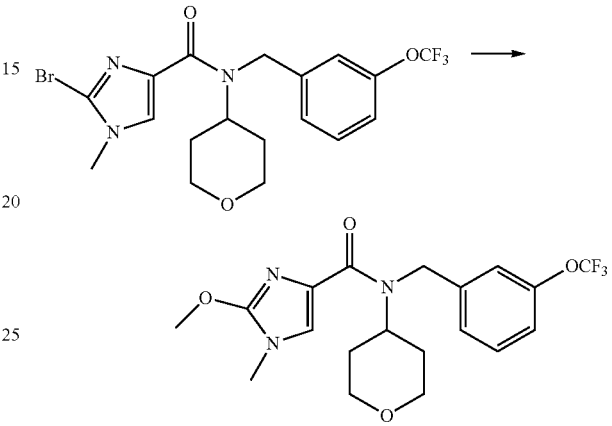

A mixture of 2-bromo-1-methyl-N-(tetrahydro-2H-pyran-4-yl)-N-[3-(trifluoromethoxy)benzyl]-1H-imidazole-4-carboxamide (100 mg), sodium methoxide (14 mg) and tetrahydrofuran (1 mL) was stirred at 60° C. for 3 days. The reaction mixture was concentrated under reduced pressure and the resulting residue was purified by column chromatography (NH silica gel cartridge; hexane/ethyl acetate=3:1 to 1:1) and TLC (NH silica gel plate; hexane/ethyl acetate=1:1) to give the titled compound (6 mg).

EXAMPLE 5

N-[2-(4-Chlorophenoxy)ethyl]-1-methyl-N-(tetrahydro-2H-pyran-4-yl)-1H-imidazole-4-carboxamide

[Formula 20]

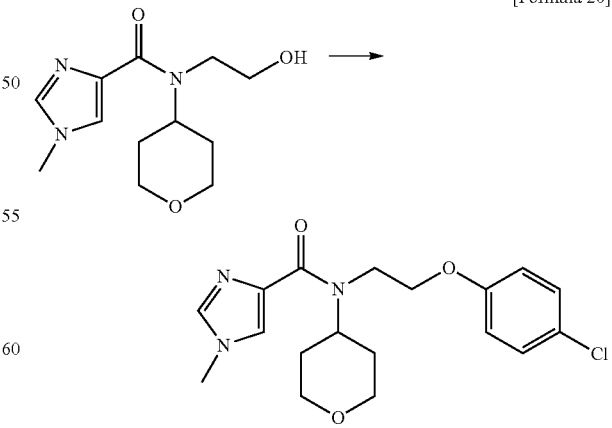

To a mixture of N-(2-hydroxyethyl)-1-methyl-N-(tetrahydro-2H-pyran-4-yl)-1H-imidazole-4-carboxamide (150 mg), p-chlorophenol (114 mg), triphenylphosphine (217 mg) and tetrahydrofuran (3.8 mL), DIAD (172 μL) was added under cooling with ice and the resulting mixture was stirred at room temperature for 3 days. To the reaction mixture, water was added and extraction was conducted with diethyl ether. The diethyl ether layer was dried over anhydrous sodium sulfate. After filtering off the desiccant, the solvents were distilled off under reduced pressure and the resulting residue was purified by column chromatography (silica gel cartridge; chloroform/methanol=99:1 and NH silica gel cartridge; hexane/ethyl acetate=1:3 to 1:9) to give the titled compound (103 mg).

EXAMPLE 6

N-(Tetrahydro-2H-pyran-4-yl)-N-[3-(trifluoromethoxy)benzyl]-5,6,7,8-tetrahydroimidazo[1,2-a]pyridine-2-carboxamide

[Formula 21]

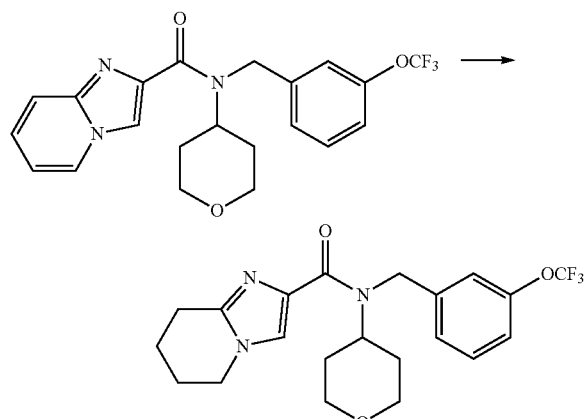

A mixture of N-(tetrahydro-2H-pyran-4-yl)-N-[3-(trifluoromethoxy)benzyl]imidazo[1,2-a]pyridine-2-carboxamide (50 mg), 10% palladium-carbon (50 mg) and methanol (15 mL) was stirred in a nitrogen atmosphere for 2 hours at room temperature. The insoluble matter was filtered off and methanol was distilled off under reduced pressure to give the titled compound (48 mg).

EXAMPLE 7

N-[(6-Fluorobiphenyl-3-yl)methyl]-1-methyl-N-(tetrahydro-2H-pyran-4-yl)-1H-imidazole-4-carboxamide

[Formula 22]

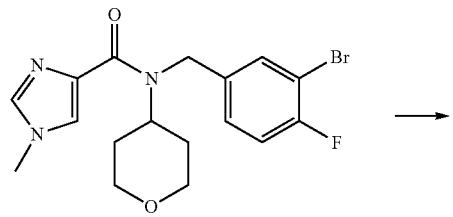

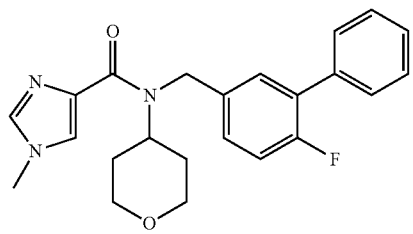

A mixture of N-(3-bromo-4-fluorobenzyl)-1-methyl-N-(tetrahydro-2H-pyran-4-yl)-1H-imidazole-4-carboxamide (150 mg), phenylboronic acid (92 mg), tetrakis(triphenylphosphine)palladium (50 mg), potassium carbonate (110 mg), DMF (2 mL) and ethanol (1 mL) was subjected to reaction in a microwave reactor (150° C., 10 min). Water was added to the reaction mixture, followed by extraction with ethyl acetate and concentrating under reduced pressure. The resulting residue was purified by TLC (silica gel) (chloroform:methanol=10:1) to give the titled compound (50 mg).

EXAMPLE 8

N-[3-(1H-Imidazol-1-yl)benzyl]-1-methyl-N-(tetrahydro-2H-pyran-4-yl)-1H-1,2,4-triazole-3-carboxamide

[Formula 23]

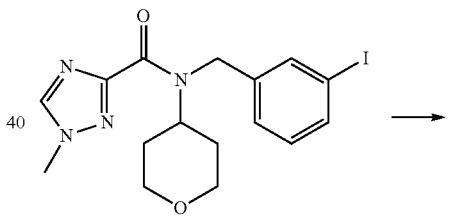

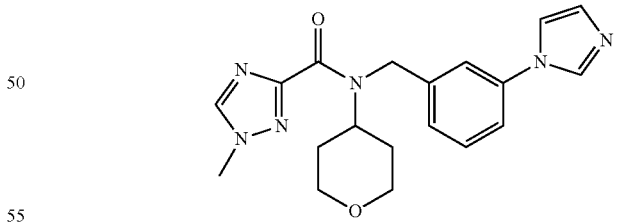

A mixture of N-(3-iodobenzyl)-1-methyl-N-(tetrahydro-2H-pyran-4-yl)-1H-1,2,4-triazole-3-carboxamide (100 mg), imidazole (38 mg), copper iodide (9 mg), cesium carbonate (321 mg), 1,2-diaminocyclohexane (23 μL) and dioxane (1 mL) was stirred overnight at 120° C. After being left to cool, the mixture was diluted with chloroform, and the chloroform layer was washed with 12% aqueous ammonia and saturated saline, and dried over anhydrous magnesium sulfate. After filtering off the desiccant, the solvents were distilled off under reduced pressure and the resulting residue was purified by column chromatography (NH silica gel cartridge; hexane, ethyl acetate, chloroform/methanol=100:0 to 90:10) to give the titled compound (17 mg).

EXAMPLE 9

Methyl N-[(1-methyl-1H-imidazol-4-yl)carbonyl]-N-(tetrahydro-2H-pyran-4-yl)-3-(trifluoromethoxy)phenylalaninate

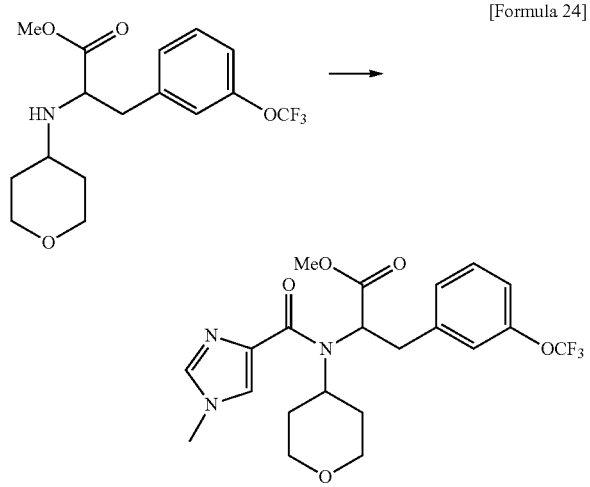

[Formula 24]

To a mixture of 1-methyl-1H-imidazole-4-carboxylic acid (500 mg) and chloroform (5 mL), oxalyl chloride (0.6 mL) was added in a nitrogen atmosphere. A drop of DMF was added to the resulting mixture, which was stirred for 2 hours at room temperature. The reaction mixture was concentrated under reduced pressure to give a solid (670 mg). The solid (31 mg) was added to methyl N-(tetrahydro-2H-pyran-4-yl)-3-(trifluoromethoxy)phenylalaninate (50 mg), diisopropylethylamine (51 μL) and chloroform (0.5 mL) and the resulting mixture was stirred for 12 hours at room temperature. The reaction mixture was concentrated under reduced pressure and the resulting residue was purified by column chromatography (NH silica gel cartridge; hexane/ethyl acetate=95:5 to 0:100) to give the titled compound (19 mg).

EXAMPLE 10

N-[1-Hydroxy-3-[3-(trifluoromethoxy)phenyl]propan-2-yl]-1-methyl-N-(tetrahydro-2H-pyran-4-yl)-1H-imidazole-4-carboxamide

[Formula 25]

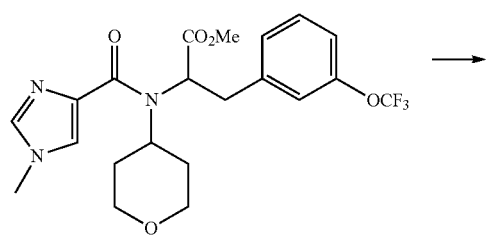

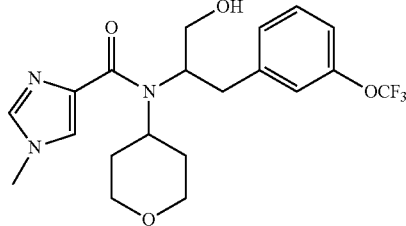

To a solution of methyl N-[(1-methyl-1H-imidazol-4-yl)carbonyl]-N-(tetrahydro-2H-pyran-4-yl)-3-(trifluoromethoxy)phenylalaninate (55 mg) in ethanol (2.2 mL), sodium borohydride (23 mg) was added and the resulting mixture was heated under reflux for 3 hours. To the ice-cooled reaction mixture, 1 M HCl was added dropwise and the resulting mixture was stirred for 30 minutes at room temperature. After adding water, the mixture was subjected to extraction with ethyl acetate. The organic layer was dried over anhydrous sodium sulfate. After filtering off the desiccant, the filtrate was concentrated under reduced pressure and the resulting residue was purified by TLC (silica gel plate; chloroform/methanol=10:1) and column chromatography (NH silica gel cartridge; chloroform) to give the titled compound (4.9 mg).

EXAMPLE 11

N-[[6-Fluoro-3'-(hydroxymethyl)biphenyl-3-yl]methyl]-1-methyl-N-(tetrahydro-2H-pyran-4-yl)-1H-1,2,4-triazole-3-carboxamide

[Formula 26]

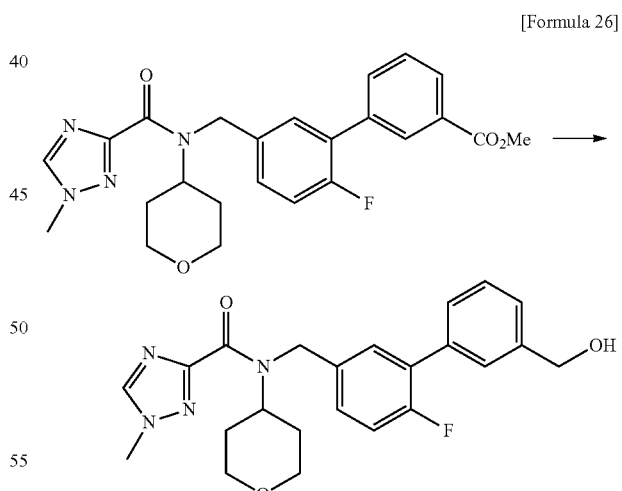

A mixture of methyl 2'-fluoro-5'-([[(1-methyl-1H-1,2,4-triazol-3-yl)carbonyl](tetrahydro-2H-pyran-4-yl)amino]methyl)biphenyl-3-carboxylate (318 mg), ethanol (14 mL) and sodium borohydride (532 mg) was heated under reflux for 16 hours. After leaving the mixture to cool, water-acetone was added and extraction was conducted with chloroform. The organic layer was dried over anhydrous sodium sulfate. After filtering off the desiccant, the solvents were distilled off under reduced pressure and the resulting residue was purified by

EXAMPLE 12

N-[[6-Fluoro-3'-(hydroxymethyl)biphenyl-3-yl]methyl]-1-methyl-N-(tetrahydro-2H-pyran-4-yl)-1H-1,2,4-triazole-3-carboxamide

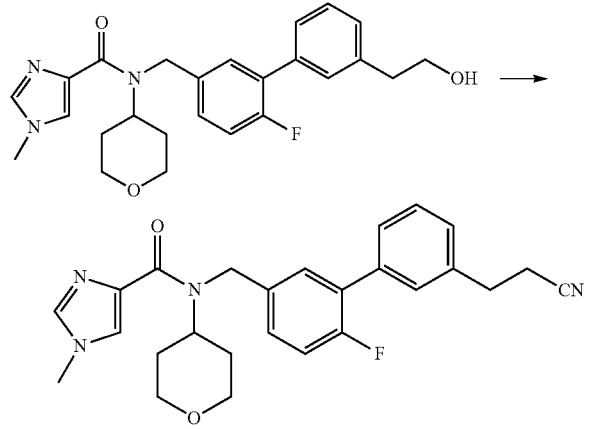

To a mixture of N-[[6-fluoro-3'-(2-hydroxyethyl)biphenyl-3-yl]methyl]-1-methyl-N-(tetrahydro-2H-pyran-4-yl)-1H-imidiazole-4-carboxamide (266 mg), triethylamine (0.1 mL) and chloroform (3.0 mL), methane sulfonylchloride (49 µL) was added and the resulting mixture was stirred for half an hour at room temperature. To the reaction mixture, water and chloroform were added and the chloroform layer was separated by means of a phase separator and concentrated under reduced pressure. The resulting residue was dissolved in dimethylformamide (9.3 mL) and after adding potassium cyanide (362 mg), the resulting mixture was stirred for 10 hours at 100° C. To the reaction mixture, water and chloroform were added and the chloroform layer, as separated by means of the phase separator, was concentrated under reduced pressure. The resulting residue was purified by TLC (NH silica gel plate; ethyl acetate) to give the titled compound (197 mg).

EXAMPLE 13

N-[[6-Fluoro-4'-(trifluoromethoxy)biphenyl-3-yl]methyl]-1-methyl-N-(tetrahydro-2H-thiopyran-4-yl)-1H-imidiazole-4-carboxamide

[Formula 28]

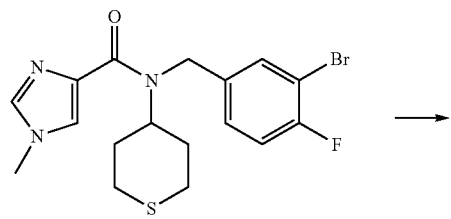

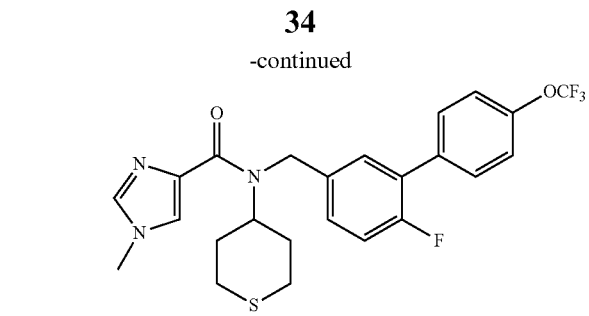

A mixture of N-(3-bromo-4-fluorobenzyl)-1-methyl-N-(tetrahydro-2H-thiopyran-4-yl)-1H-imidiazole-4-carboxamide (412 mg), 4-trimethoxyphenylboronic acid (227 mg), tetrakis(triphenylphosphine)palladium (110 mg), cesium carbonate (326 mg), toluene (4 mL), ethanol (4 mL) and water (2.6 mL) was subjected to reaction in a microwave reactor (150° C., 30 min). To the reaction mixture, water was added and following extraction with ethyl acetate, the extract was concentrated under reduced pressure. The resulting residue was purified by column chromatography (NH silica gel cartridge; hexane/ethyl acetate=100:0 to 1:1) to give the titled compound (442 mg).

EXAMPLE 14

1-Methyl-N-[3-methyl-5-(trifluoromethoxy)benzyl]-N-(tetrahydro-2H-thiopyran-4-yl)-1H-imidiazole-4-carboxamide

[Formula 29]

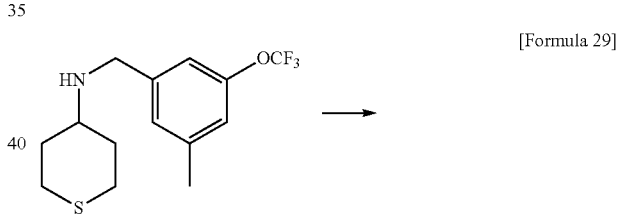

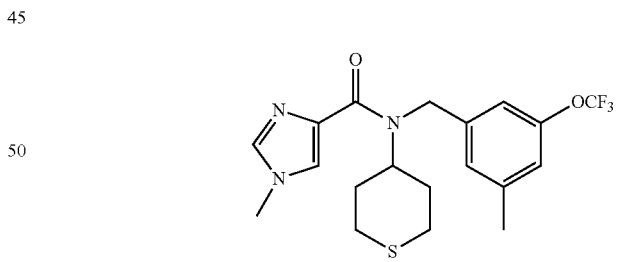

A mixture of N-[3-methyl-5-(trifluoromethoxy)benzyl] tetrahydro-2H-thiopyran-4-amine (830 mg), 1-methyl-1H-imidazole-4-carboxylic acid (380 mg), EDC.HCl (860 mg), HOBt (460 mg), dimethylformamide (20 mL) and triethylamine (0.94 mL) was stirred overnight at room temperature. The solvents were distilled off under reduced pressure and extraction was conducted with ethyl acetate; the organic layer was washed with a saturated aqueous solution of sodium hydrogencarbonate and saturated saline and dried over anhydrous magnesium sulfate. After filtering off the desiccant, the solvent was concenrated. The residue was purified by column

EXAMPLE 15

N-(1,1-Dioxidetetrahydro-2H-thiopyran-4-yl)-N-[[6-fluoro-4'-(trifluoromethoxy)biphenyl]-3-yl]methyl]-1-methyl-1H-imidiazole-4-carboxamide

[Formula 30]

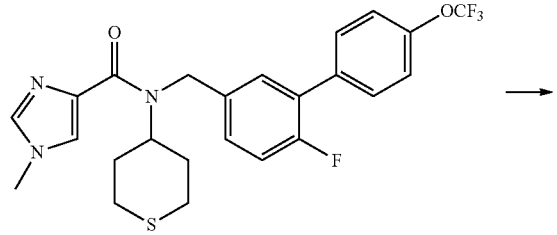

→

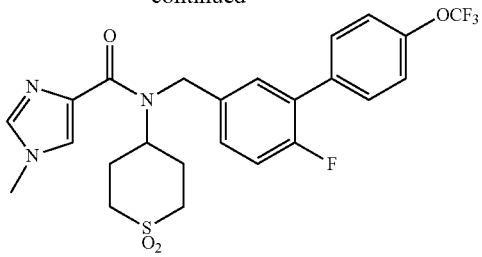

To a mixture of N-[[6-fluoro-4'-(trifluoromethoxy)biphenyl]-3-yl]methyl]-1-methyl-N-(tetrahydro-2H-thiopyran-4-yl)-1H-imidiazole-4-carboxamide (200 mg) and ethanol (3 mL), meta-chloroperbenzoic acid (156 mg) was added and the resulting mixture was stirred overnight at room temperature. A saturated aqueous solution of sodium thiosulfate was added and the resulting mixture was stirred for an hour at room temperature. Following extraction with ethyl acetate, the organic layer was washed with saturated saline and dried over anhydrous sodium sulfate. After filtering off the desiccant, the solvents were distilled off under reduced pressure and the resulting residue was purified by preparative HPLC to give the titled compound (167 mg).

The structural formulas and instrument data for the compounds described in Examples 1 to 15 and the compounds synthesized by similar methods to the ones employed in Examples 1 to 15 are shown in Table 1, Tables 2-1 to 2-12, as well as Tables 3-1 and 3-2. The numbers indicated in the "Example" column of each table refer to which of Examples 1 to 15 were based upon to synthesize the relevant compounds.

TABLE 1

| Compound | Example | Structure | NMR | (ESI pos.) m/z |
|---|---|---|---|---|
| 1 | 1 | 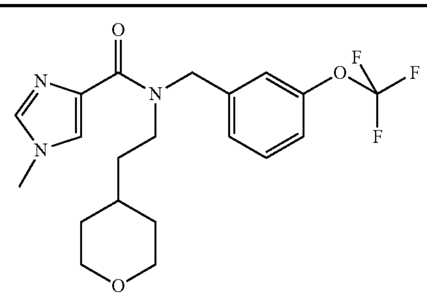 | 1H NMR (600 MHz, CHLOROFORM-d) d ppm 1.20-1.35 (m, 3H) 1.54-1.70 (m, 4H) 3.23-5.49 (m, 11H) 7.05-7.64 (m, 6H) | 412 ([M + H]+) |
| 2 | 2 | 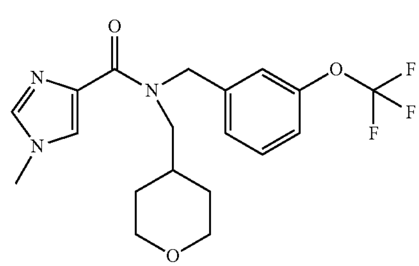 [SMILES: Cn1cnc(C(=O)N(Cc2cccc(OC(F)(F)F)c2)CC2CCOCC2)c1] | 1H NMR (600 MHz, CHLOROFORM-d) d ppm 1.26-1.66 (m, 4H) 1.86-2.09 (s, 1H) 3.22-3.38 (m, 3H) 3.66-4.09 (m, 6H) 4.71-5.50 (m, 2H) 7.06-7.21 (m, 3H) 7.29-7.40 (m, 2H) 7.59 (s, 1H) | 398 ([M + H]+) |
| 3 | 3 | 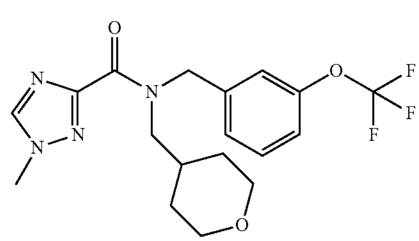 [SMILES: Cn1cnc(C(=O)N(Cc2cccc(OC(F)(F)F)c2)CC2CCOCC2)n1] | 1H NMR (600 MHz, CHLOROFORM-d) d ppm 1.10-2.13 (m, 5H) 3.21-3.66 (m, 4H) 3.86-4.04 (m, 5H) 4.74-5.02 (m, 2H) 7.08-7.42 (m, 4H) 7.97-8.13 (m, 1H) | 399 ([M + H]+) |

TABLE 1-continued

| Compound | Example | Structure | NMR | (ESI pos.) m/z |
|---|---|---|---|---|
| 4 | 3 | (3-chlorophenyl ethyl)-N-(tetrahydropyran-4-yl)-1-methyl-1H-1,2,4-triazole-3-carboxamide | 1H NMR (600 MHz, CHLOROFORM-d) δ ppm 1.53-1.95 (m, 7H) 3.22-3.37 (m, 2H) 3.97 (s, 5H) 4.13-5.64 (m, 2H) 7.27-8.18 (m, 5H) | 349 ([M + H]+) |

The compounds listed in Tables 2-1 to 2-12 are represented by the following formula [II], with Ar⁴ and Ar⁵ being defined in the relevant tables.

[Formula 31]

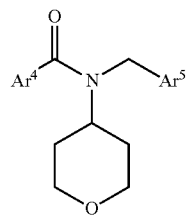

[II]

TABLE 2-1

| Compound | Example | Ar⁴ | Ar⁵ | NMR | (ESI pos.) m/z (ESI neg.) m/z |
|---|---|---|---|---|---|
| 5 | 6 | 5,6,7,8-tetrahydroimidazo[1,2-a]pyridin-2-yl | 3-(trifluoromethoxy)phenyl | 1H NMR (600 MHz, CHLOROFORM-d) d ppm 1.58-2.10 (m, 8H) 2.62-2.98 (m, 2H) 3.37-3.51 (m, 2H) 3.87-4.09 (m, 6H) 4.51-5.82 (m, 3H) 6.99-7.52 (m, 5H) | 423 ([M + H]+) |
| 6 | 2 | 2-bromo-1-methyl-1H-imidazol-4-yl | 3-(trifluoromethoxy)phenyl | 1H NMR (600 MHz, CHLOROFORM-d) d ppm 1.60-1.91 (m, 4H) 3.24-4.03 (m, 7H) 4.60-5.18 (m, 3H) 6.95-7.63 (m, 5H) | 462 ([M + H]+) |
| 7 | 4 | 2-methoxy-1-methyl-1H-imidazol-4-yl | 3-(trifluoromethoxy)phenyl | 1H NMR (600 MHz, CHLOROFORM-d) d ppm 1.61-1.87 (m, 4H) 3.25-4.20 (m, 10H) 4.63-5.28 (m, 3H) 6.94-7.60 (m, 5H) | 414 ([M + H]+) |
| 8 | 2 | 2-methyl-1H-imidazol-4-yl | 3-(trifluoromethoxy)phenyl | 1H NMR (600 MHz, CHLOROFORM-d) d ppm 1.61-1.90 (m, 4H) 2.42 (br. s., 3H) 3.41-3.53 (m, 2H) 3.93-4.05 (m, 2H) 4.65-5.05 (m, 3H) 6.98-7.41 (m, 5H) | 384 ([M + H]+) |

TABLE 2-1-continued

| Compound | Example | Ar⁴ | Ar⁵ | NMR | (ESI pos.) m/z (ESI neg.) m/z |
|---|---|---|---|---|---|
| 9 | 3 | 2,1-dimethylimidazole | 3-(OCF₂F)phenyl | 1H NMR (600 MHz, CHLOROFORM-d) d ppm 1.50-1.90 (m, 4H) 2.13-2.52 (m, 3H) 3.37-3.50 (m, 2H) 3.57 (br. s., 3H) 3.89-4.02 (m, 2H) 4.48-5.81 (m, 3H) 7.00-7.56 (m, 5H) | 398 ([M + H]+) |
| 10 | 1 | 1-methylimidazole | 3-(OCF₂F)phenyl | 1H NMR (600 MHz, CHLOROFORM-d) d ppm 1.66-1.87 (m, 4H) 3.35-3.51 (m, 2H) 3.70 (br. s., 3H) 3.87-4.03 (m, 2H) 4.57-5.71 (m, 3H) 6.99-7.64 (m, 6H) | 384 ([M + H]+) |
| 11 | 1 | imidazole (NH) | 3-(OCF₂F)phenyl | 1H NMR (600 MHz, CHLOROFORM-d) d ppm 1.72-1.95 (m, 4H) 3.36-3.54 (m, 2H) 3.88-4.06 (m, 2H) 4.60-5.63 (m, 3H) 6.96-7.75 (m, 6H) 10.59-11.22 (m, 1H) | 370 ([M + H]+) 368 ([M − H]−) |
| 12 | 1 | 1-cyclopropylimidazole | 3-(OCF₂F)phenyl | 1H NMR (600 MHz, CHLOROFORM-d) d ppm 0.87-1.12 (m, 4H) 1.64-1.91 (m, 4H) 3.24-4.06 (m, 5H) 4.59-5.65 (m, 3H) 7.00-7.74 (m, 6H) | 410 ([M + H]+) |

TABLE 2-2

| Compound | Example | Ar⁴ | Ar⁵ | NMR | (ESI pos.) m/z (ESI neg.) m/z |
|---|---|---|---|---|---|
| 13 | 3 | 1-ethylimidazole | 3-(OCF₂F)phenyl | 1H NMR (600 MHz, CHLOROFORM-d) d ppm 1.40-1.52 (m, 3H) 1.68-1.87 (m, 4H) 3.40-3.51 (m, 2H) 3.90-5.71 (m, 5H) 7.03-7.69 (m, 6H) | 398 ([M + H]+) |
| 14 | 3 | 1-(2,2,2-trifluoroethyl)imidazole | 3-(OCF₂F)phenyl | 1H NMR (600 MHz, CHLOROFORM-d) d ppm 1.67-1.89 (m, 4H) 3.39-3.52 (m, 2H) 3.92-4.01 (m, 2H) 4.39-5.60 (m, 5H) 6.84-7.58 (m, 6H) | 452 ([M + H]+) |
| 15 | 1 | 1-methylimidazole | 3-chlorophenyl | 1H NMR (600 MHz, CHLOROFORM-d) d ppm 1.64-1.89 (m, 4H) 3.36-3.51 (m, 2H) 3.71 (br. s., 3H) 3.89-4.00 (m, 2H) 4.55-5.71 (m, 3H) 7.07-7.43 (m, 5H) 7.58 (s, 1H) | 334 ([M + H]+) |
| 16 | 1 | 1-methylimidazole | 3-(CF₃)phenyl | 1H NMR (600 MHz, CHLOROFORM-d) d ppm 1.63-1.94 (m, 4H) 3.37-3.53 (m, 2H) 3.71 (br. s., 3H) 3.89-4.02 (m, 2H) 4.62-5.74 (m, 3H) 7.15-7.66 (m, 6H) | 368 ([M + H]+) |

TABLE 2-2-continued

| Compound | Example | Ar⁴ | Ar⁵ | NMR | (ESI pos.) m/z (ESI neg.) m/z |
|---|---|---|---|---|---|
| 17 | 1 | 1-methyl-imidazol-4-yl | 2-(trifluoromethoxy)phenyl | 1H NMR (600 MHz, CHLOROFORM-d) δ ppm 1.63-1.89 (m, 4H) 3.38-3.51 (m, 2H) 3.61-3.83 (m, 3H) 3.89-4.01 (m, 2H) 4.63-5.68 (m, 3H) 7.13-7.67 (m, 6H) | 276 ([M + H]+) |
| 18 | 1 | 1-methyl-imidazol-4-yl | phenoxymethyl | 1H NMR (600 MHz, CHLOROFORM-d) δ ppm 1.67-1.84 (m, 2H) 1.90-2.09 (m, 2H) 3.37-5.54 (m, 12H) 6.81-7.02 (m, 3H) 7.19-7.61 (m, 4H) | 330 ([M + H]+) |
| 19 | 1 | 1H-1,2,4-triazol-3-yl | 3-(trifluoromethoxy)phenyl | 1H NMR (600 MHz, CHLOROFORM-d) δ ppm 1.58-1.95 (m, 4H) 3.39-3.59 (m, 2H) 3.93-4.07 (m, 2H) 4.64-5.98 (m, 3H) 7.01-8.36 (m, 6H) | 371 ([M + H]+) |
| 20 | 3 | 1-(2-methoxyethyl)-imidazol-4-yl | 3-(trifluoromethoxy)phenyl | 1H NMR (600 MHz, CHLOROFORM-d) δ ppm 1.58-1.87 (m, 4H) 3.24-3.73 (m, 6H) 3.90-4.18 (m, 5H) 4.64-5.73 (m, 3H) 7.01-7.76 (m, 6H) | 428 ([M + H]+) |

TABLE 2-3

| Compound | Example | Ar⁴ | Ar⁵ | NMR | (ESI pos.) m/z (ESI neg.) m/z |
|---|---|---|---|---|---|
| 21 | 3 | 1-propyl-imidazol-4-yl | 3-(trifluoromethoxy)phenyl | 1H NMR (600 MHz, CHLOROFORM-d) δ ppm 0.78-1.06 (m, 3H) 1.65-1.97 (m, 4H) 3.30-3.54 (m, 2H) 3.75-4.08 (m, 6H) 4.56-5.80 (m, 3H) 6.92-7.74 (m, 5H) | 412 ([M + H]+) |
| 22 | 3 | 1-methyl-1,2,4-triazol-3-yl | 3-(trifluoromethoxy)phenyl | 1H NMR (600 MHz, CHLOROFORM-d) δ ppm 1.68-1.90 (m, 4H) 3.31-3.54 (m, 2H) 3.91-4.15 (m, 5H) 4.70-5.03 (m, 3H) 6.99-7.97 (m, 5H) | 385 ([M + H]+) |
| 23 | 1 | 1-methyl-imidazol-4-yl | 3-methoxyphenyl | 1H NMR (600 MHz, CHLOROFORM-d) δ ppm 1.65-1.95 (m, 4H) 3.37-3.50 (m, 2H) 3.60-3.85 (m, 6H) 3.88-4.01 (m, 2H) 4.50-5.73 (m, 3H) 6.69-6.94 (m, 3H) 7.13-7.63 (m, 3H) | 330 ([M + H]+) |
| 24 | 1 | 1-methyl-imidazol-4-yl | 3-chloro-4-fluorophenyl | 1H NMR (600 MHz, CHLOROFORM-d) δ ppm 1.63-1.90 (m, 4H) 3.37-3.54 (m, 2H) 3.72 (br. s, 3H) 3.89-4.03 (m, 2H) 4.45-5.69 (m, 3H) 6.97-7.49 (m, 4H) 7.59 (s, 1H) | 352 ([M + H]+) |

TABLE 2-3-continued

| Compound | Example | Ar⁴ | Ar⁵ | NMR | (ESI pos.) m/z (ESI neg.) m/z |
|---|---|---|---|---|---|
| 25 | 1 | 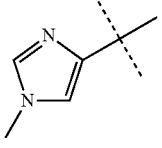 | 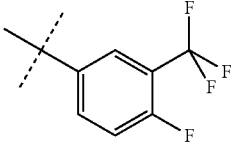 | 1H NMR (600 MHz, CHLOROFORM-d) d ppm 1.62-1.90 (m, 4H) 3.38-3.51 (m, 2H) 3.72 (br. s., 3H) 3.90-4.02 (m, 2H) 4.54-5.72 (m, 3H) 7.04-7.55 (m, 4H) 7.59 (s, 1H) | 386 ([M + H]+) |
| 26 | 1 | 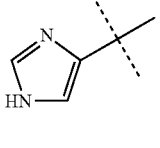 | 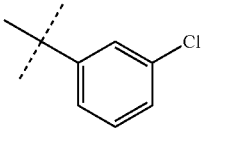 | 1H NMR (600 MHz, CHLOROFORM-d) d ppm 1.72-1.98 (m, 4H) 3.31-3.60 (m, 2H) 3.88-4.11 (m, 2H) 4.51-5.73 (m, 3H) 7.29-7.94 (m, 6H) 10.61-11.68 (m, 1H) | 320 ([M + H]+) 318 ([M − H]−) |
| 27 | 1 | 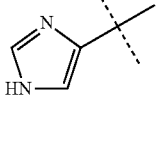 | 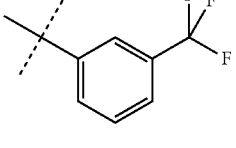 | 1H NMR (600 MHz, CHLOROFORM-d) d ppm 1.58-1.96 (m, 4H) 3.39-3.54 (m, 2H) 3.92-4.07 (m, 2H) 4.64-5.78 (m, 3H) 6.97-8.35 (m, 6H) | 354 ([M + H]+) 352 ([M − H]−) |
| 28 | 2 | 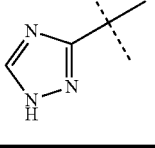 | 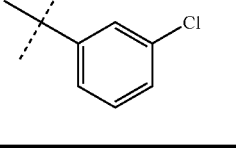 | 1H NMR (600 MHz, CHLOROFORM-d) d ppm 1.57-1.96 (m, 4H) 3.40-3.59 (m, 2H) 3.92-4.06 (m, 2H) 4.61-6.00 (m, 3H) 7.04-8.21 (m, 5H) | 321 ([M + H]+) 319 ([M − H]−) |

TABLE 2-4

| Compound | Example | Ar⁴ | Ar⁵ | NMR | (ESI pos.) m/z (ESI neg.) m/z |
|---|---|---|---|---|---|
| 29 | 2 | 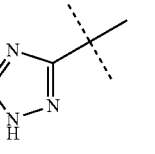 | 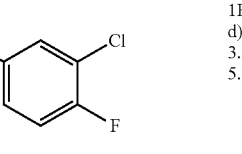 | 1H NMR (600 MHz, CHLOROFORM-d) d ppm 1.58-1.93 (m, 4H) 3.40-3.56 (m, 2H) 3.94-4.06 (m, 2H) 4.61-5.88 (m, 3H) 7.03-8.17 (m, 4H) | 339 ([M + H]+) 337 ([M − H]−) |
| 30 | 2 | 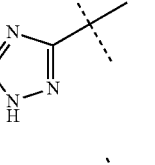 | 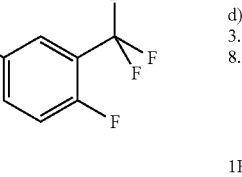 | 1H NMR (600 MHz, CHLOROFORM-d) d ppm 1.59-1.93 (m, 4H) 3.36-3.60 (m, 4H) 3.93-5.97 (m, 3H) 7.02-8.23 (m, 4H) | 373 ([M + H]+) 371 ([M − H]−) |
| 31 | 2 | 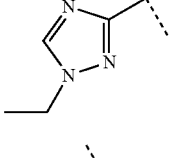 | 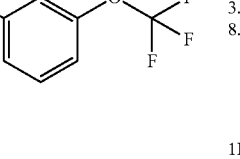 | 1H NMR (600 MHz, CHLOROFORM-d) d ppm 1.37-1.91 (m, 7H) 3.22-3.56 (m, 2H) 3.87-4.99 (m, 7H) 7.02-8.19 (m, 5H) | 399 ([M + H]+) |
| 32 | 3 | 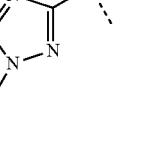 | 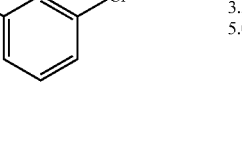 | 1H NMR (600 MHz, CHLOROFORM-d) d ppm 1.66-1.93 (m, 4H) 3.29-3.56 (m, 2H) 3.90-4.17 (m, 5H) 4.66-5.00 (m, 3H) 6.97-7.97 (m, 5H) | 335 ([M + H]+) |

TABLE 2-4-continued

| Compound | Example | Ar⁴ | Ar⁵ | NMR | (ESI pos.) m/z (ESI neg.) m/z |
|---|---|---|---|---|---|
| 33 | 3 | 1-methyl-1,2,4-triazol-3-yl | 3-(trifluoromethyl)phenyl | 1H NMR (600 MHz, CHLOROFORM-d) d ppm 1.62-1.86 (m, 4H) 3.22-3.55 (m, 2H) 3.84-4.07 (m, 5H) 4.48-5.01 (m, 3H) 7.35-8.17 (m, 4H) | 369 ([M + H]+) |
| 34 | 3 | 1-methyl-1,2,4-triazol-3-yl | 3-chloro-4-fluorophenyl | 1H NMR (600 MHz, CHLOROFORM-d) d ppm 1.59-1.88 (m, 2H) 3.22-3.53 (m, 2H) 3.86-4.06 (m, 5H) 4.44-4.92 (m, 3H) 6.99-8.16 (m, 4H) | 353 ([M + H]+) |
| 35 | 3 | 1-methyl-1,2,4-triazol-3-yl | 4-fluoro-3-(trifluoromethyl)phenyl | 1H NMR (600 MHz, CHLOROFORM-d) d ppm 1.59-1.89 (m, 4H) 3.24-3.53 (m, 2H) 3.85-4.06 (m, 5H) 4.52-4.94 (m, 3H) 7.09-8.17 (m, 4H) | 387 ([M + H]+) |
| 36 | 5 | 1-methyl-imidazol-4-yl | (4-chlorophenoxy)methyl | 1H NMR (600 MHz, CHLOROFORM-d) d ppm 1.66-2.04 (m, 4H) 3.38-3.84 (m, 7H) 3.97-4.09 (m, 2H) 4.18 (t, J = 6.42 Hz, 3H) 6.77-6.93 (m, 2H) 7.16-7.24 (m, 2H) 7.30-7.59 (m, 2H) | 364 ([M + H]+) |

TABLE 2-5

| Compound | Example | Ar⁴ | Ar⁵ | NMR | (ESI pos.) m/z (ESI neg.) m/z |
|---|---|---|---|---|---|
| 37 | 5 | 1-methyl-imidazol-4-yl | (3-chlorophenoxy)methyl | 1H NMR (600 MHz, CHLOROFORM-d) d ppm 2.04 (s, 4H) 3.29-3.88 (m, 7H) 3.97-4.10 (m, 2H) 4.16-5.55 (m, 3H) 6.73-7.22 (m, 3H) 7.37 (s, 2H) | 364 ([M + H]+) |
| 38 | 5 | 1-methyl-imidazol-4-yl | (2-chlorophenoxy)methyl | 1H NMR (600 MHz, CHLOROFORM-d) d ppm 1.67-2.18 (m, 4H) 3.30-3.94 (m, 7H) 3.96-4.09 (m, 2H) 4.30 (s, 3H) 6.82-7.24 (m, 3H) 7.29-7.60 (m, 3H) | 364 ([M + H]+) |
| 39 | 5 | 1-methyl-imidazol-4-yl | (3,4-dichlorophenoxy)methyl | 1H NMR (600 MHz, CHLOROFORM-d) d ppm 1.67-2.03 (m, 4H) 3.72 (s, 7H) 3.98-4.10 (m, 2H) 4.14-5.54 (m, 3H) 6.72-7.20 (m, 2H) 7.27-7.61 (m, 3H) | 398 ([M + H]+) |
| 40 | 2 | 1-methyl-imidazol-4-yl | (2-chlorophenyl)methyl | 1H NMR (600 MHz, CHLOROFORM-d) d ppm 1.63-2.13 (m, 4H) 3.01-3.18 (m, 2H) 3.33-3.66 (m, 3H) 3.73 (s, 3H) 3.87-4.16 (m, 3H) 4.62-5.51 (m, 1H) 7.10-7.23 (m, 2H) 7.52 (s, 4H) | 348 ([M + H]+) |

TABLE 2-5-continued

| Compound | Example | Ar⁴ | Ar⁵ | NMR | (ESI pos.) m/z (ESI neg.) m/z |
|---|---|---|---|---|---|
| 41 | 1 | 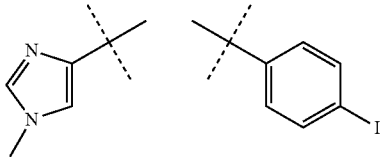 | 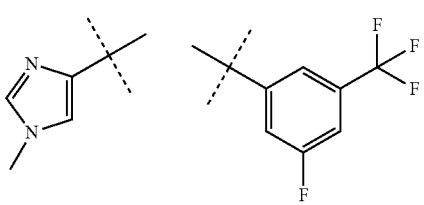 | 1H NMR (600 MHz, CHLOROFORM-d) d ppm 1.62-1.87 (m, 4H) 3.36-3.50 (m, 2H) 3.71 (br. s., 3H) 3.88-4.00 (m, 2H) 4.54-5.65 (m, 3H) 6.93-7.12 (m, 2H) 7.31-7.66 (m, 4H) | 426 ([M + H]+) |
| 42 | 1 | 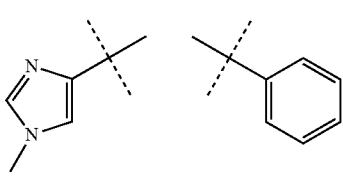 | 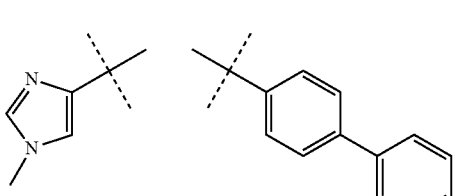 | 1H NMR (600 MHz, CHLOROFORM-d) d ppm 1.65-1.92 (m, 4H) 3.40-3.54 (m, 2H) 3.72 (br. s., 3H) 3.91-4.04 (m, 2H) 4.60-5.77 (m, 3H) 7.11-7.64 (m, 5H) | 386 ([M + H]+) |
| 43 | 2 | | | 1H NMR (600 MHz, CHLOROFORM-d) d ppm 1.66-1.91 (m, 4H) 3.34-3.51 (m, 2H) 3.71 (br. s., 3H) 3.87-3.98 (m, 2H) 4.56-5.68 (m, 3H) 7.11-7.63 (m, 7H) | 300 ([M + H]+) |
| 44 | 2 | | | 1H NMR (600 MHz, CHLOROFORM-d) d ppm 1.63-1.94 (m, 4H) 3.40-3.51 (m, 2H) 3.63-3.80 (m, 3H) 3.91-4.01 (m, 2H) 4.58-5.70 (m, 3H) 7.18-7.73 (m, 11H) | 376 ([M + H]+) |

TABLE 2-6

| Compound | Example | Ar⁴ | Ar⁵ | NMR | (ESI pos.) m/z (ESI neg.) m/z |
|---|---|---|---|---|---|
| 45 | 3 | 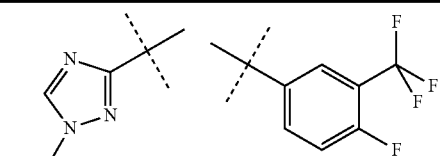 | | 1H NMR (600 MHz, CHLOROFORM-d) d ppm 1.40-1.89 (m, 7H) 3.25-3.54 (m, 2H) 3.90-4.97 (m, 7H) 7.04-8.19 (m, 4H) | 401 ([M + H]+) |
| 46 | 3 | 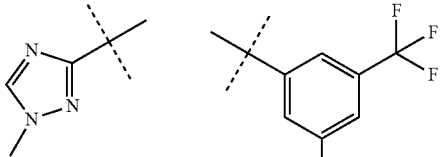 | | 1H NMR (600 MHz, CHLOROFORM-d) d ppm 1.63-1.90 (m, 4H) 3.23-3.58 (m, 2H) 3.85-4.08 (m, 5H) 4.55-5.06 (m, 3H) 7.11-7.42 (m, 3H) 7.89-8.18 (m, 1H) | 387 ([M + H]+) |
| 47 | 3 | 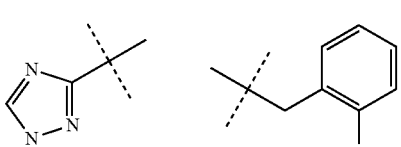 | | 1H NMR (600 MHz, CHLOROFORM-d) d ppm 1.64-2.06 (m, 4H) 2.99-3.73 (m, 6H) 3.93-4.11 (m, 5H) 4.29-4.81 (m, 1H) 7.10-7.41 (m, 4H) 8.04-8.10 (m, 1H) | 349 ([M + H]+) |

TABLE 2-6-continued

| Compound | Example | Ar⁴ | Ar⁵ | NMR | (ESI pos.) m/z (ESI neg.) m/z |
|---|---|---|---|---|---|
| 48 | 1 | 3-tert-butyl-1H-1,2,4-triazole | 4-fluoro-3-(trifluoromethoxy)phenyl | 1H NMR (600 MHz, CHLOROFORM-d) d ppm 1.55-1.95 (m, 4H) 3.33-3.56 (m, 2H) 3.93-5.78 (m, 5H) 7.06-7.31 (m, 3H) 8.01-8.28 (m, 1H) | 389 ([M + H]+) 387 ([M − H]−) |
| 49 | 3 | 1-methyl-3-tert-butyl-1,2,4-triazole | 4-fluoro-3-(trifluoromethoxy)phenyl | 1H NMR (600 MHz, CHLOROFORM-d) d ppm 1.60-1.91 (m, 4H) 3.21-3.56 (m, 2H) 3.83-4.10 (m, 5H) 4.47-4.93 (m, 3H) 7.07-7.35 (m, 3H) 7.89-8.17 (m, 1H) | 403 ([M + H]+) |
| 50 | 3 | 1-methyl-3-tert-butyl-1,2,4-triazole | 3,5-dichlorophenyl | 1H NMR (600 MHz, CHLOROFORM-d) d ppm 1.64-1.92 (m, 4H) 3.22-3.58 (m, 2H) 3.86-4.09 (m, 5H) 4.52-5.00 (m, 3H) 7.10-7.32 (m, 3H) 7.91-8.18 (m, 1H) | 369 ([M + H]+) |
| 51 | 3 | 1-methyl-3-tert-butyl-1,2,4-triazole | naphthalen-2-yl | 1H NMR (600 MHz, CHLOROFORM-d) d ppm 1.63-1.93 (m, 4H) 3.19-3.53 (m, 2H) 3.81-4.09 (m, 5H) 4.42-4.88 (m, 1H) 4.90-5.14 (m, 2H) 7.35-8.16 (m, 8H) | 351 ([M + H]+) |
| 52 | 3 | 1-methyl-3-tert-butyl-1,2,4-triazole | 4-(trifluoromethoxy)phenyl | 1H NMR (600 MHz, CHLOROFORM-d) d ppm 1.60-1.92 (m, 4H) 3.21-3.54 (m, 2H) 3.87-4.08 (m, 5H) 4.42-4.95 (m, 3H) 7.07-8.16 (m, 5H) | 385 ([M + H]+) |

TABLE 2-7

| Compound | Example | Ar⁴ | Ar⁵ | NMR | (ESI pos.) m/z (ESI neg.) m/z |
|---|---|---|---|---|---|
| 53 | 3 | 1-methyl-3-tert-butyl-1,2,4-triazole | 3-iodophenyl | 1H NMR (600 MHz, CHLOROFORM-d) d ppm 1.62-1.86 (m, 4H) 3.21-3.53 (m, 2H) 3.87-4.06 (m, 5H) 4.46-4.93 (m, 3H) 6.97-8.15 (m, 5H) | 427 ([M + H]+) |
| 54 | 3 | 1-methyl-3-tert-butyl-1,2,4-triazole | 4-fluoro-3-methoxyphenyl | 1H NMR (600 MHz, CHLOROFORM-d) d ppm 1.61-1.92 (m, 4H) 3.20-3.54 (m, 2H) 3.78-4.07 (m, 8H) 4.36-4.90 (m, 3H) 6.71-7.07 (m, 3H) 7.93-8.14 (m, 1H) | 349 ([M + H]+) |
| 55 | 7 | 1-methyl-3-tert-butyl-1,2,4-triazole | biphenyl-3-yl | 1H NMR (600 MHz, CHLOROFORM-d) d ppm 1.64-1.94 (m, 4H) 3.20-3.55 (m, 2H) 3.83-4.07 (m, 5H) 4.43-5.02 (m, 3H) 7.19-8.18 (m, 10H) | 377 ([M + H]+) |

TABLE 2-7-continued

| Compound | Example | Ar⁴ | Ar⁵ | NMR | (ESI pos.) m/z (ESI neg.) m/z |
|---|---|---|---|---|---|
| 56 | 3 | 3-tert-butyl-1-methyl-1,2,4-triazole | 2,3-dichlorophenyl | 1H NMR (600 MHz, CHLOROFORM-d) δ ppm 1.60-1.86 (m, 4H) 3.22-3.53 (m, 2H) 3.87-4.07 (m, 5H) 4.48-4.93 (m, 3H) 7.10-8.14 (m, 4H) | 369 ([M + H]+) |
| 57 | 3 | 3-tert-butyl-1-methyl-1,2,4-triazole | 3-bromo-4-fluorophenyl | 1H NMR (600 MHz, CHLOROFORM-d) δ ppm 1.52-1.89 (m, 4H) 3.22-3.53 (m, 2H) 3.88-4.07 (m, 5H) 4.45-4.90 (m, 3H) 6.96-7.59 (m, 3H) 7.94-8.25 (m, 1H) | 397 ([M + H]+) |
| 58 | 3 | 3-tert-butyl-1-methyl-1,2,4-triazole | 3,4-difluorophenyl | 1H NMR (600 MHz, CHLOROFORM-d) δ ppm 1.63-1.86 (m, 4H) 3.21-3.56 (m, 2H) 3.86-4.09 (m, 5H) 4.45-4.89 (m, 3H) 6.94-7.24 (m, 3H) 7.93-8.15 (m, 1H) | 337 ([M + H]+) |
| 59 | 7 | 3-tert-butyl-1-methyl-1,2,4-triazole | 2-fluoro-5-phenyl-biphenyl | 1H NMR (600 MHz, CHLOROFORM-d) δ ppm 1.64-1.94 (m, 4H) 3.22-3.53 (m, 2H) 3.86-4.07 (m, 5H) 4.91 (s, 3H) 6.91-7.62 (m, 8H) 7.94-8.24 (m, 1H) | 395 ([M + H]+) |
| 60 | 7 | 3-tert-butyl-1-methyl-1,2,4-triazole | 4'-chloro-2-fluorobiphenyl | 1H NMR (600 MHz, CHLOROFORM-d) δ ppm 1.61-1.96 (m, 4H) 3.23-3.53 (m, 2H) 3.85-4.07 (m, 5H) 4.44-4.95 (m, 3H) 6.93-7.55 (m, 7H) 7.95-8.13 (m, 1H) | 429 ([M + H]+) |

TABLE 2-8

| Compound | Example | Ar⁴ | Ar⁵ | NMR | (ESI pos.) m/z (ESI neg.) m/z |
|---|---|---|---|---|---|
| 61 | 7 | 3-tert-butyl-1-methyl-1,2,4-triazole | 3'-chloro-2-fluorobiphenyl | 1H NMR (600 MHz, CHLOROFORM-d) δ ppm 1.53-1.96 (m, 4H) 3.21-3.56 (m, 2H) 3.84-4.12 (m, 5H) 4.45-5.14 (m, 3H) 6.91-7.75 (m, 7H) 7.93-8.21 (m, 1H) | 429 ([M + H]+) |
| 62 | 3 | 3-tert-butyl-1-methyl-1,2,4-triazole | 3-phenoxyphenyl | 1H NMR (600 MHz, CHLOROFORM-d) δ ppm 1.62-1.88 (m, 4H) 3.22-3.53 (m, 2H) 3.85-4.05 (m, 5H) 4.40-4.93 (m, 3H) 6.79-7.37 (m, 9H) 7.92-8.13 (m, 1H) | 393 ([M + H]+) |
| 63 | 3 | 3-tert-butyl-1-methyl-1,2,4-triazole | 4-fluoro-3-(trifluoromethoxy)phenyl | 1H NMR (600 MHz, CHLOROFORM-d) δ ppm 1.61-1.87 (m, 4H) 3.25-3.54 (m, 2H) 3.85-4.07 (m, 5H) 4.54-5.01 (m, 3H) 6.99-7.37 (m, 3H) 7.94-8.23 (m, 1H) | 403 ([M + H]+) |

TABLE 2-8-continued

| Compound | Example | Ar⁴ | Ar⁵ | NMR | (ESI pos.) m/z (ESI neg.) m/z |
|---|---|---|---|---|---|
| 64 | 3 | 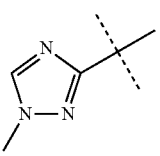 | 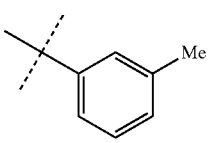 | 1H NMR (600 MHz, CHLOROFORM-d) d ppm 1.62-1.91 (m, 4H) 2.27-2.36 (m, 3H) 3.20-3.52 (m, 2H) 3.86-4.06 (m, 5H) 4.38-5.04 (m, 3H) 6.98-7.22 (m, 4H) 7.91-8.11 (m, 1H) | 315 ([M + H]+) |
| 65 | 3 | 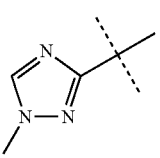 | 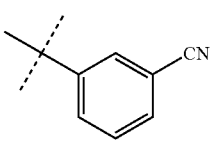 | 1H NMR (600 MHz, CHLOROFORM-d) d ppm 1.62-1.88 (m, 4H) 3.25-3.55 (m, 2H) 3.87-4.07 (m, 5H) 4.54-5.24 (m, 3H) 7.37-7.66 (m, 4H) 7.92-8.15 (m, 1H) | 326 ([M + H]+) |
| 66 | 3 | 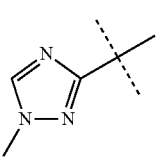 | 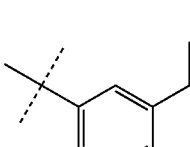 | 1H NMR (600 MHz, CHLOROFORM-d) d ppm 1.63-1.95 (m, 4H) 3.19-3.53 (m, 2H) 3.84-4.07 (m, 5H) 4.40-5.04 (m, 3H) 7.68-8.13 (m, 5H) 8.62-8.77 (m, 1H) | 378 ([M + H]+) |
| 67 | 3 | 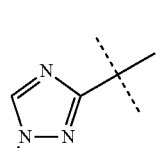 | 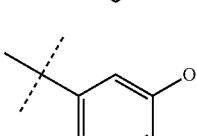 | 1H NMR (600 MHz, CHLOROFORM-d) d ppm 1.63-1.93 (m, 4H) 3.23-3.53 (m, 2H) 3.87-4.07 (m, 5H) 4.46-5.15 (m, 3H) 6.34-6.65 (m, 1H) 6.93-7.35 (m, 4H) 7.92-8.22 (m, 1H) | 367 ([M + H]+) |
| 68 | 3 | 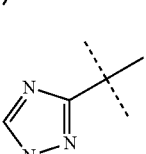 | 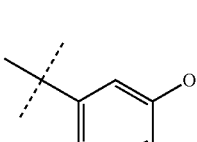 | 1H NMR (600 MHz, CHLOROFORM-d) d ppm 1.63-1.90 (m, 4H) 3.23-3.55 (m, 2H) 3.83-4.08 (m, 5H) 4.46-4.93 (m, 3H) 6.32-6.69 (m, 2H) 7.11-7.26 (m, 3H) 7.92-8.14 (m, 1H) | 433 ([M + H]+) |

TABLE 2-9

| Compound | Example | Ar⁴ | Ar⁵ | NMR | (ESI pos.) m/z (ESI neg.) m/z |
|---|---|---|---|---|---|
| 69 | 3 | 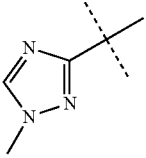 | 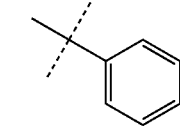 | 1H NMR (600 MHz, CHLOROFORM-d) d ppm 1.61-1.91 (m, 4H) 3.25-3.53 (m, 2H) 3.86-4.06 (m, 5H) 4.50-4.93 (m, 3H) 7.12-7.43 (m, 4H) 7.91-8.14 (m, 1H) | 419 ([M + H]+) |
| 70 | 2 | 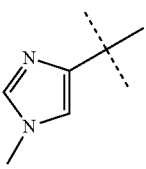 | 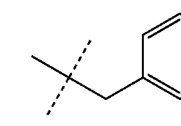 | 1H NMR (600 MHz, CHLOROFORM-d) d ppm 1.69-1.99 (m, 4H) 2.94-3.04 (m, 2H) 3.37-3.66 (m, 3H) 3.73 (s, 3H) 3.92-4.18 (m, 3H) 4.68-5.52 (m, 1H) 7.03-7.25 (m, 3H) 7.53 (s, 3H) | 398 ([M + H]+) |
| 71 | 7 | 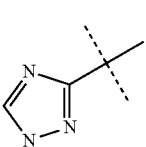 | 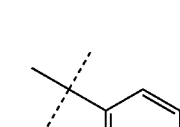 | 1H NMR (600 MHz, CHLOROFORM-d) d ppm 1.66-1.93 (m, 4H) 3.24-3.52 (m, 2H) 3.86-4.05 (m, 5H) 4.49-5.39 (m, 3H) 7.28-7.70 (m, 5H) 7.82-8.13 (m, 2H) 8.55-8.63 (m, 1H) 8.78-8.86 (m, 1H) | 378 ([M + H]+) |

TABLE 2-9-continued

| Compound | Example | Ar⁴ | Ar⁵ | NMR | (ESI pos.) m/z (ESI neg.) m/z |
|---|---|---|---|---|---|
| 72 | 7 | | | 1H NMR (600 MHz, CHLOROFORM-d) d ppm 1.63-1.93 (m, 4H) 3.19-3.54 (m, 2H) 3.85-4.07 (m, 5H) 4.48-5.02 (m, 3H) 7.30-8.72 (m, 9H) | 378 ([M + H]+) |
| 73 | 3 | | | 1H NMR (600 MHz, CHLOROFORM-d) d ppm 1.63-1.89 (m, 4H) 3.24-3.56 (m, 2H) 3.84-4.09 (m, 5H) 4.54-4.98 (m, 3H) 7.03-7.33 (m, 3H) 7.90-8.16 (m, 1H) | 419 ([M + H]+) |
| 74 | 8 | | | 1H NMR (600 MHz, CHLOROFORM-d) d ppm 1.64-1.91 (m, 4H) 3.23-3.51 (m, 2H) 3.85-4.05 (m, 5H) 4.48-4.99 (m, 3H) 7.15-8.12 (m, 8H) | 367 ([M + H]+) |
| 75 | 3 | | | 1H NMR (600 MHz, CHLOROFORM-d) d ppm 1.63-1.88 (m, 4H) 3.20-3.33 (m, 1H) 3.42-3.52 (m, 1H) 3.89-4.02 (m, 2H) 4.23-4.35 (m, 1H) 4.79 (d, J = 11.92 Hz, 3H) 7.03-7.46 (m, 6H) 8.37-8.67 (m, 1H) | 421 ([M + H]+) |
| 76 | 7 | | | 1H NMR (600 MHz, CHLOROFORM-d) d ppm 1.62-1.94 (m, 4H) 3.21-3.51 (m, 2H) 3.86-4.06 (m, 5H) 4.40-5.11 (m, 3H) 7.01-7.23 (m, 1H) 7.98 (s, 3H) | 385 ([M + H]+) |

TABLE 2-10

| Compound | Example | Ar⁴ | Ar⁵ | NMR | (ESI pos.) m/z (ESI neg.) m/z |
|---|---|---|---|---|---|
| 77 | 7 | | | 1H NMR (600 MHz, CHLOROFORM-d) d ppm 1.65-1.91 (m, 4H) 3.24-3.33 (m, 1H) 3.43-3.51 (m, 1H) 3.88-4.05 (m, 8H) 4.46-4.96 (m, 3H) 7.01-7.13 (m, 1H) 7.27-8.23 (m, 7H) | 453 ([M + H]+) |
| 78 | 11 | | | 1H NMR (600 MHz, CHLOROFORM-d) d ppm 1.62-1.92 (m, 4H) 3.21-3.34 (m, 1H) 3.42-3.53 (m, 1H) 3.87-4.04 (m, 5H) 4.76 (d, J = 3.67 Hz, 5H) 7.02-7.12 (m, 1H) 7.20-8.13 (m, 7H) | 423 ([M − H]−) |

TABLE 2-10-continued

| Compound | Example | Ar⁴ | Ar⁵ | NMR | (ESI pos.) m/z (ESI neg.) m/z |
|---|---|---|---|---|---|
| 79 | 7 | 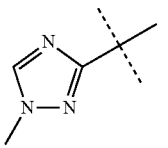 | 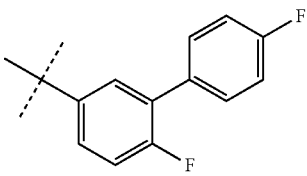 | 1H NMR (600 MHz, CHLOROFORM-d) d ppm 1.59-1.93 (m, 4H) 3.22-3.35 (m, 1H) 3.40-3.53 (m, 1H) 3.86-4.04 (m, 5H) 4.46-4.95 (m, 3H) 7.02-7.16 (m, 3H) 7.18-8.14 (m, 5H) | 413 ([M + H]+) |
| 80 | 3 | 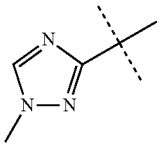 | 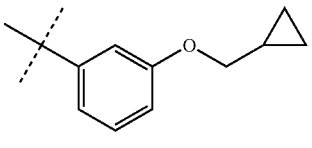 | 1H NMR (600 MHz, CHLOROFORM-d) d ppm 0.29-0.40 (m, 2H) 0.56-0.69 (m, 2H) 1.20-1.32 (m, 1H) 1.62-1.91 (m, 4H) 3.19-3.51 (m, 2H) 3.71-4.07 (m, 7H) 4.37-4.92 (m, 3H) 6.70-7.23 (m, 4H) 7.91-8.14 (m, 1H) | 371 ([M + H]+) |
| 81 | 2 | 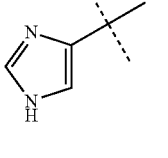 | 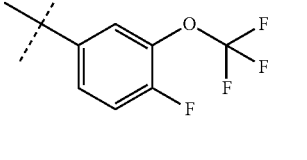 | 1H NMR (600 MHz, CHLOROFORM-d) d ppm 1.52-2.02 (m, 4H) 3.40-3.60 (m, 2H) 3.90-4.14 (m, 2H) 4.52-5.74 (m, 3H) 7.02-7.88 (m, 5H) | 488 ([M + H]+) 486 ([M − H]−) |
| 82 | 3 | 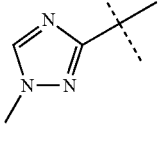 | 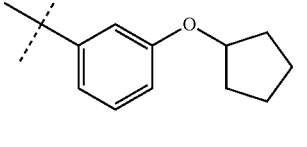 | 1H NMR (600 MHz, CHLOROFORM-d) d ppm 1.52-1.96 (m, 12H) 3.20-3.53 (m, 2H) 3.83-4.07 (m, 5H) 4.37-4.92 (m, 4H) 6.67-7.22 (m, 4H) 7.91-8.14 (m, 1H) | 385 ([M + H]+) |
| 83 | 3 | 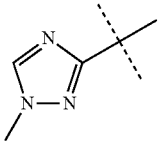 | 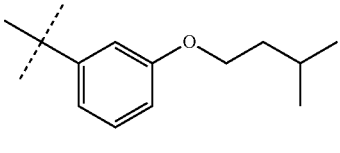 | 1H NMR (600 MHz, CHLOROFORM-d) d ppm 0.92-0.99 (m, 6H) 1.62-1.89 (m, 7H) 3.21-3.50 (m, 2H) 3.86-4.03 (m, 7H) 4.38-4.91 (m, 3H) 6.71-7.23 (m, 4H) 7.93-8.12 (m, 1H) | 387 ([M + H]+) |
| 84 | 7 | 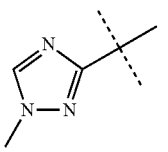 | 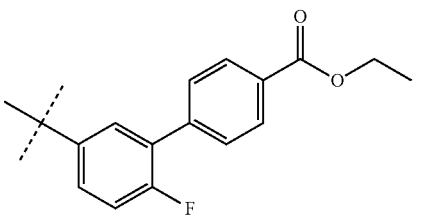 | 1H NMR (600 MHz, CHLOROFORM-d) d ppm 1.41 (t, J = 7.34 Hz, 3H) 1.63-1.94 (m, 4H) 3.23-3.34 (m, 1H) 3.43-3.51 (m, 1H) 3.87-4.06 (m, 5H) 4.41 (d, J = 7.34 Hz, 2H) 4.46-4.97 (m, 3H) 7.05-7.14 (m, 1H) 7.27-8.16 (m, 7H) | 453 ([M + H]+) |
| 85 | 11 | 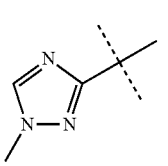 | 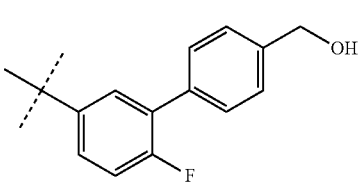 | 1H NMR (600 MHz, CHLOROFORM-d) d ppm 1.62-1.93 (m, 4H) 3.24-3.33 (m, 1H) 3.43-3.51 (m, 1H) 3.86-4.04 (m, 5H) 4.47-4.94 (m, 5H) 7.04-7.12 (m, 1H) 7.20-8.12 (m, 7H) | 425 ([M + H]+) |
| 86 | 7 | 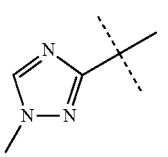 | 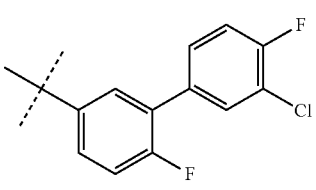 | 1H NMR (600 MHz, CHLOROFORM-d) d ppm 1.63-1.91 (m, 4H) 3.24-3.52 (m, 2H) 3.87-4.05 (m, 5H) 4.46-4.94 (m, 3H) 7.04-8.14 (m, 7H) | 447 ([M + H]+) |

TABLE 2-11

| Compound | Example | Ar⁴ | Ar⁵ | NMR | (ESI pos.) m/z (ESI neg.) m/z |
|---|---|---|---|---|---|
| 87 | 7 | 1-methyl-1,2,4-triazol-3-yl | 5-(2-fluoro-4'-(trifluoromethoxy)biphenyl) | 1H NMR (600 MHz, CHLOROFORM-d) d ppm 1.64-1.91 (m, 4H) 3.23-3.53 (m, 2H) 3.86-4.05 (m, 5H) 4.47-4.94 (m, 3H) 7.06-7.51 (m, 8H) | 479 ([M + H]+) |
| 88 | 7 | 1-methyl-1,2,4-triazol-3-yl | 2',6-difluorobiphenyl | 1H NMR (600 MHz, CHLOROFORM-d) d ppm 1.60-1.92 (m, 4H) 3.24-3.52 (m, 2H) 3.86-4.05 (m, 5H) 4.47-4.96 (m, 3H) 7.05-8.12 (m, 8H) | 413 ([M + H]+) |
| 89 | 7 | 1-methyl-1,2,4-triazol-3-yl | 2-fluoro-4'-(trifluoromethoxy)biphenyl | 1H NMR (600 MHz, CHLOROFORM-d) d ppm 1.63-1.92 (m, 4H) 3.24-3.53 (m, 2H) 3.87-4.06 (m, 5H) 4.47-4.95 (m, 3H) 7.04-8.15 (m, 8H) | 479 ([M + H]+) |
| 90 | 7 | 1-methyl-1,2,4-triazol-3-yl | 2'-chloro-6-fluorobiphenyl | 1H NMR (600 MHz, CHLOROFORM-d) d ppm 1.64-1.92 (m, 4H) 3.23-3.53 (m, 2H) 3.86-4.05 (m, 5H) 4.46-4.96 (m, 3H) 7.04-7.50 (m, 7H) 7.94-8.11 (m, 1H) | 429 ([M + H]+) |
| 91 | 7 | 1-methyl-1,2,4-triazol-3-yl | 3'-ethoxy-6-fluorobiphenyl | 1H NMR (600 MHz, CHLOROFORM-d) d ppm 1.43 (t, J = 7.11 Hz, 3H) 1.62-1.91 (m, 4H) 3.22-3.33 (m, 1H) 3.43-3.51 (m, 1H) 3.87-4.04 (m, 5H) 4.08 (q, J = 7.11 Hz, 2H) 4.45-4.93 (m, 3H) 6.86-8.13 (m, 8H) | 439 ([M + H]+) |
| 92 | 7 | 1-methyl-1,2,4-triazol-3-yl | 2',4'-dichloro-6-fluorobiphenyl | 1H NMR (600 MHz, CHLOROFORM-d) d ppm 1.61-1.92 (m, 4H) 3.22-3.33 (m, 1H) 3.42-3.52 (m, 1H) 3.86-4.05 (m, 5H) 4.45-4.94 (m, 3H) 7.26 (s, 7H) | 463 ([M + H]+) |
| 93 | 7 | 1-methyl-1,2,4-triazol-3-yl | 6-fluoro-3'-propoxybiphenyl | 1H NMR (600 MHz, CHLOROFORM-d) d ppm 1.05 (t, J = 7.57 Hz, 3H) 1.63-1.92 (m, 6H) 3.23-3.33 (m, 1H) 3.42-3.53 (m, 1H) 3.88-4.04 (m, 5H) 4.44-4.94 (m, 3H) 6.88-8.13 (m, 8H) | 453 ([M + H]+) |
| 94 | 7 | 1-methylimidazol-4-yl | 6-fluoro-3'-(hydroxymethyl)biphenyl | 1H NMR (600 MHz, CHLOROFORM-d) d ppm 1.58-1.91 (m, 4H) 3.37-3.51 (m, 2H) 3.71 (br. s., 3H) 3.88-4.03 (m, 2H) 4.75 (d, J = 5.50 Hz, 5H) 7.00-7.11 (m, 1H) 7.16-7.67 (m, 8H) | 424 ([M + H]+) 422 ([M − H]−) |

TABLE 2-11-continued

| Compound | Example | Ar⁴ | Ar⁵ | NMR | (ESI pos.) m/z (ESI neg.) m/z |
|---|---|---|---|---|---|
| 95 | 7 | 3-methyl-1H-1,2,4-triazol-5-yl | 5-substituted-2-fluorophenyl-3'-(trifluoromethyl)biphenyl | 1H NMR (600 MHz, CHLOROFORM-d) d ppm 1.63-1.91 (m, 4H) 3.23-3.35 (m, 1H) 3.42-3.52 (m, 1H) 3.87-4.05 (m, 5H) 4.46-4.95 (m, 3H) 7.26 (s, 8H) | 463 ([M + H]+) |
| 96 | 7 | 3-methyl-1H-1,2,4-triazol-5-yl | 5-substituted-2-fluorophenyl-3'-phenoxybiphenyl | 1H NMR (600 MHz, CHLOROFORM-d) d ppm 1.63-1.82 (m, 4H) 3.22-3.33 (m, 1H) 3.41-3.54 (m, 1H) 3.85-4.06 (m, 5H) 4.46-4.97 (m, 3H) 6.99-8.19 (m, 13H) | 487 ([M + H]+) |

TABLE 2-12

| Compound | Example | Ar⁴ | Ar⁵ | NMR | (ESI pos.) m/z (ESI neg.) m/z |
|---|---|---|---|---|---|
| 97 | 7 | 3-methyl-1H-1,2,4-triazol-5-yl | 5-substituted-2-fluorophenyl-2',4',6'-trifluorobiphenyl | 1H NMR (600 MHz, CHLOROFORM-d) d ppm 1.62-1.88 (m, 4H) 3.20-3.31 (m, 1H) 3.39-3.52 (m, 1H) 3.86-4.06 (m, 5H) 4.36-4.91 (m, 3H) 6.92-8.15 (m, 6H) | |
| 98 | 7 | 3-methyl-1H-1,2,4-triazol-5-yl | 5-substituted-2-fluorophenyl-4'-(trifluoromethyl)biphenyl | 1H NMR (600 MHz, CHLOROFORM-d) d ppm 1.63-1.93 (m, 4H) 3.24-3.34 (m, 1H) 3.41-3.52 (m, 1H) 3.86-4.05 (m, 5H) 4.47-4.95 (m, 3H) 6.93-8.15 (m, 8H) | 463 ([M + H]+) |
| 99 | 7 | 1-methyl-1H-imidazol-4-yl | 5-substituted-2-fluorophenyl-3'-(2-hydroxyethyl)biphenyl | 1H NMR (600 MHz, CHLOROFORM-d) d ppm 1.39-1.93 (m, 4H) 2.88-2.95 (m, 2H) 3.37-4.00 (m, 9H) 4.59-5.63 (m, 2H) 7.01-7.24 (m, 3H) 7.27-7.59 (m, 6H) | 438 ([M + H]+) |
| 100 | 7 | 1-methyl-1H-imidazol-4-yl | 5-substituted-2-fluorophenyl-4'-(trifluoromethoxy)biphenyl | 1H NMR (600 MHz, METHANOL-d3) d ppm 1.67-1.77 (m, 2H) 1.90-2.04 (m, 2H) 3.44-3.56 (m, 2H) 3.82-4.05 (m, 5H) 4.36-4.65 (m, 1H) 7.14-7.72 (m, 8H) 9.01 (br. s., 1H) | 478 ([M + H]+) |
| 101 | 12 | 1-methyl-1H-imidazol-4-yl | 5-substituted-2-fluorophenyl-3'-(2-cyanoethyl)biphenyl | 1H NMR (600 MHz, CHLOROFORM-d) d ppm 1.60-1.90 (m, 4H) 3.07-3.14 (m, 2H) 3.38-3.99 (m, 9H) 4.58-5.61 (m, 3H) 6.99-8.03 (m, 9H) | 447 ([M + H]+) |

TABLE 2-12-continued

| Compound | Example | Ar⁴ | Ar⁵ | NMR | (ESI pos.) m/z (ESI neg.) m/z |
|---|---|---|---|---|---|
| 102 | 2 | 1-methyl-imidazol-4-yl | 2-bromo-4-fluorophenyl | 1H NMR (600 MHz, CHLOROFORM-d) d ppm 1.63-1.90 (m, 4H) 3.38-3.51 (m, 2H) 3.72 (s, 3H) 3.89-4.02 (m, 2H) 4.48-5.73 (m, 3H) 6.96-7.63 (m, 5H) | 396, 398 ([M + H]+) |
| 103 | 7 | 1-methyl-imidazol-4-yl | 2-fluoro-4'-fluorobiphenyl | 1H NMR (600 MHz, CHLOROFORM-d) d ppm 1.67-1.90 (m, 4H) 3.40-3.50 (m, 2H) 3.72 (s, 3H) 3.91-4.00 (m, 2H) 4.62-5.66 (m, 3H) 7.02-7.61 (m, 9H) | 412 ([M + H]+) |
| 104 | 7 | 1-methyl-imidazol-4-yl | 2-fluoro-4'-trifluoromethylbiphenyl | 1H NMR (600 MHz, CHLOROFORM-d) d ppm 1.69-1.93 (m, 4H) 3.36-3.51 (m, 2H) 3.71 (s, 3H) 3.89-4.01 (m, 2H) 4.60-5.65 (m, 3H) 7.02-7.72 (m, 9H) | 462 ([M + H]+) |
| 105 | 7 | 1-methyl-imidazol-4-yl | 2-fluoro-4'-methylbiphenyl | 1H NMR (600 MHz, CHLOROFORM-d) d ppm 1.66-1.91 (m, 4H) 2.39 (s, 3H) 3.38-3.48 (m, 2H) 3.70 (s, 3H) 3.90-4.02 (m, 2H) 4.55-5.72 (m, 3H) 6.99-7.71 (m, 9H) | 408 ([M + H]+) |
| 106 | 7 | 1-methyl-imidazol-4-yl | 4-phenoxyphenyl | 1H NMR (600 MHz, CHLOROFORM-d) d ppm 1.66-1.91 (m, 4H) 3.39-3.48 (m, 2H) 3.65-3.76 (m, 3H) 3.90-4.02 (m, 2H) 4.61-5.64 (m, 3H) 6.87-7.61 (m, 9H) | 392 ([M + H]+) |

TABLE 3-1

| Compound | Example | Structure | NMR | (ESI pos.) m/z (ESI neg.) m/z |
|---|---|---|---|---|
| 107 | 9 | (1-methyl-imidazole-4-carbonyl)-N-(tetrahydropyran-4-yl)-N-[1-(methoxycarbonyl)-2-(3-trifluoromethoxyphenyl)ethyl]amide | 1H NMR (600 MHz, CHLOROFORM-d) d ppm 0.85-1.13 (m, 2H) 1.60-1.94 (m, 2H) 3.23-3.68 (m, 4H) 3.68-4.00 (m, 8H) 5.33-5.47 (m, 1H) 7.03-7.17 (m, 3H) 7.26-7.59 (m, 3H) | 456 ([M + H]+) |

TABLE 3-1-continued

| Compound | Example | Structure | NMR | (ESI pos.) m/z (ESI neg.) m/z |
|---|---|---|---|---|
| 108 | 9 | 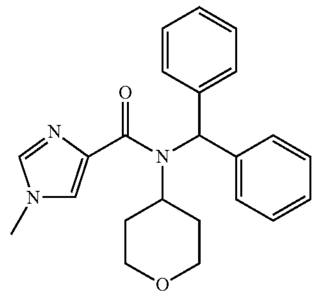 [SMILES: Cn1cnc(C(=O)N(C2CCOCC2)C(c2ccccc2)c2ccccc2)c1] | | 376 ([M + H]+) 374 ([M − H]−) |
| 109 | 10 | 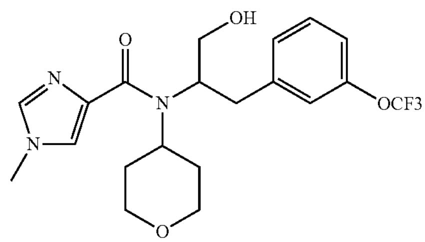 [SMILES: Cn1cnc(C(=O)N(C2CCOCC2)C(CO)Cc2cccc(OC(F)(F)F)c2)c1] | 1H NMR (600 MHz, CHLOROFORM-d) d ppm 1.21-1.43 (m, 4H) 1.57-1.77 (m, 2H) 3.19-3.58 (m, 4H) 3.74 (s, 3H) 3.76-4.16 (m, 3H) 4.97-5.57 (m, 2H) 7.04-7.20 (m, 2H) 7.27-7.58 (m, 3H) | 428 ([M + H]+) |
| 110 | 2 | 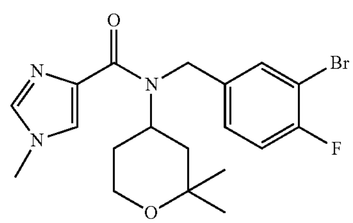 [SMILES: Cn1cnc(C(=O)N(Cc2ccc(F)c(Br)c2)C2CCOC(C)(C)C2)c1] | 1H NMR (600 MHz, CHLOROFORM-d) d ppm 1.20 (s, 3H) 1.25 (s, 3H) 1.42-1.71 (m, 4H) 3.56-3.84 (m, 5H) 4.36-6.02 (m, 3H) 6.93-7.25 (m, 2H) 7.29-7.62 (m, 3H) | 424, 426 ([M + H]+) |
| 111 | 2 | 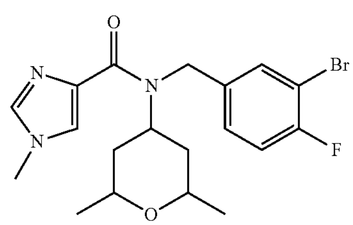 [SMILES: CC1CC(N(Cc2ccc(F)c(Br)c2)C(=O)c2cn(C)cn2)CC(C)O1] | 1H NMR (600 MHz, CHLOROFORM-d) d ppm 1.17 (s, 3H) 1.18 (s, 3H) 1.29-1.38 (m, 2H) 1.67-1.84 (m, 2H) 3.49-3.58 (m, 2H) 3.72 (s, 3H) 4.50-5.70 (m, 3H) 6.99-7.22 (m, 2H) 7.27-7.59 (m, 3H) | 424, 426 ([M + H]+) |
| 112 | 13 | 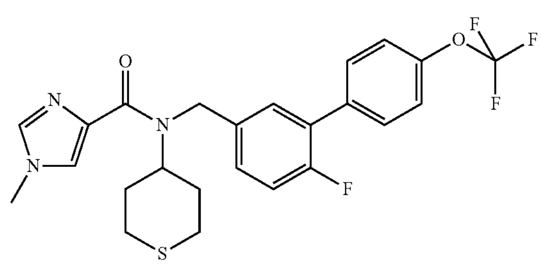 [SMILES: Cn1cnc(C(=O)N(Cc2ccc(F)c(-c3ccc(OC(F)(F)F)cc3)c2)C2CCSCC2)c1] | 1H NMR (600 MHz, CHLOROFORM-d) d ppm 1.79-2.22 (m, 4H) 2.56-2.86 (m, 4H) 3.65-3.78 (m, 3H) 4.43-5.43 (m, 3H) 7.02-7.86 (m, 9H) | 494 ([M + H]+) |
| 113 | 14 | 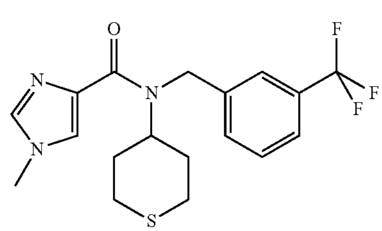 [SMILES: Cn1cnc(C(=O)N(Cc2cccc(C(F)(F)F)c2)C2CCSCC2)c1] | 1H NMR (600 MHz, CHLOROFORM-d) d ppm 1.73-2.22 (m, 4H) 2.55-2.86 (m, 4H) 3.62-3.81 (m, 3H) 4.44-5.50 (m, 3H) 7.33-7.64 (m, 6H) | 384 ([M + H]+) |

TABLE 3-2

| Compound | Example | Structure | NMR | (ESI pos.) m/z |
|---|---|---|---|---|
| 114 | 13 | 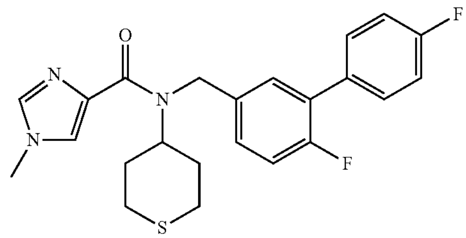 [SMILES: Cn1cnc(C(=O)N(Cc2ccc(F)c(-c3ccc(F)cc3)c2)C2CCSCC2)c1] | 1H NMR (600 MHz, CHLOROFORM-d) d ppm 1.79-2.21 (m, 4H) 2.56-2.85 (m, 4H) 3.66-3.78 (m, 3H) 4.42-5.44 (m, 3H) 7.01-7.71 (m, 9H) | 428 ([M + H]+) |
| 115 | 15 | 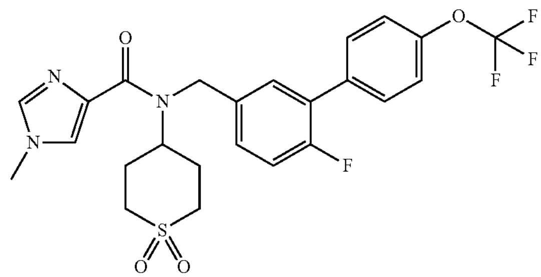 [SMILES: Cn1cnc(C(=O)N(Cc2ccc(F)c(-c3ccc(OC(F)(F)F)cc3)c2)C2CCS(=O)(=O)CC2)c1] | 1H NMR (600 MHz, CHLOROFORM-d) d ppm 2.09-2.47 (m, 4H) 2.95-3.25 (m, 5H) 3.65-3.83 (m, 3H) 4.63-5.88 (m, 3H) 7.02-7.71 (m, 9H) | 526 ([M + H]+) |
| 116 | 15 | 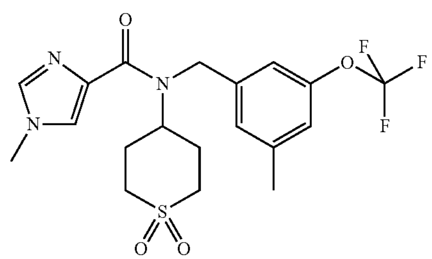 [SMILES: Cc1cc(CN(C(=O)c2cn(C)cn2)C2CCS(=O)(=O)CC2)cc(OC(F)(F)F)c1] | 1H NMR (600 MHz, CHLOROFORM-d) d ppm 1.93-2.30 (m, 4H) 3.00-3.22 (m, 6H) 3.66-3.79 (m, 4H) 4.61-5.88 (m, 3H) 6.82-7.05 (m, 4H) 7.32-7.71 (m, 2H) | 446 ([M + H]+) |
| 117 | 15 | 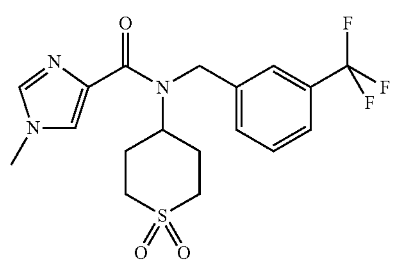 [SMILES: Cn1cnc(C(=O)N(Cc2cccc(C(F)(F)F)c2)C2CCS(=O)(=O)CC2)c1] | 1H NMR (600 MHz, CHLOROFORM-d) d ppm 1.94-2.41 (m, 4H) 2.97-3.23 (m, 4H) 3.65-3.80 (m, 3H) 4.67-5.91 (m, 3H) 7.34-7.75 (m, 6H) | 416 ([M + H]+) |
| 118 | 14 | 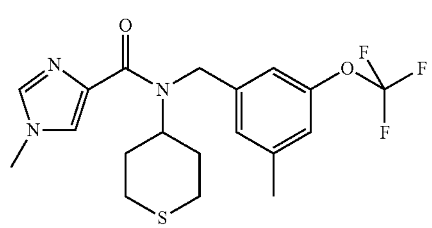 [SMILES: Cc1cc(CN(C(=O)c2cn(C)cn2)C2CCSCC2)cc(OC(F)(F)F)c1] | 1H NMR (600 MHz, CHLOROFORM-d) d ppm 1.72-2.19 (m, 4H) 2.32 (s, 3H) 2.54-2.86 (m, 4H) 3.60-3.80 (m, 3H) 4.39-5.44 (m, 3H) 6.80-7.09 (m, 3H) 7.26-7.61 (m, 2H) | 414 ([M + H]+) |

TEST EXAMPLE 1

Glycine Uptake Inhibition Experiment

A glycine uptake inhibition experiment was conducted in accordance with the method described in Neuron, 8, 927-935, 1992. Used in the experiment were T98G cells (glioma cells) developing a human type 1 glycine transporter (GlyT1). The T98G cells were seeded in a 96-well plate at a density of $2.0 \times 10^4$ cells per well and cultured overnight in a $CO_2$ incubator. The test substance was first dissolved in a 100% DMSO solution and then dissolved in a 10 mM HEPES buffer solution (pH 7.4) supplemented with 150 mM sodium chloride, 1 mM calcium chloride, 5 mM potassium chloride, 1 mM magnesium chloride, 10 mM glucose, and 0.2% bovine serum albumin. After removing the cell culture medium, the test substance was subjected to a 10-min pretreatment. Thereafter, the test substance and [$^3$H] glycine (final concentration: 250 nM) were added to the cells and reaction was performed at room temperature for 15 minutes. After the end of the reaction, the extracellular fluid was aspirated with a manifold to remove the excess marker glycine present outside of the cells; thereafter, the cells were lysed with an aqueous solution of 0.5 M sodium hydroxide. The glycine content in the cells was determined by measuring the radioactivity in the cell lysate with a liquid scintillation counter. With the amount of glycine uptake in the presence of 10 μM ALX5407 being referred to as the nonspecific uptake, the amount of specific uptake was calculated by subtracting the amount of nonspecific uptake from the total amount of uptake in the absence of 10 μM ALX5407. In addition, glycine uptake inhibiting activity ($IC_{50}$) was calculated from an inhibition curve for the concentration of the test substance ranging from $10^{-9}$ to $10^{-5}$ M.

Among the invention compounds, Nos. 5, 6, 8, 9, 12, 14, 17, 19, 20, 26, 28, 29, 30, 44, 47, 52, 63, 68, 75, 108, 111 and 117 had $IC_{50}$ values of 1 μM or more, and the other compounds had $IC_{50}$ values smaller than 1 μM. Among the compounds having $IC_{50}$ values smaller than 1 μM, Nos. 1, 2, 10, 13, 15, 16, 22 to 25, 31, 34 to 36, 39, 42, 45, 49, 53, 55, 57, 59 to 61, 67, 69, 70, 73, 77 to 79, 81, 84, 86 to 89, 91, 93 to 96, 99 to 105, 107, 109, 112 to 114 and 118 had $IC_{50}$ values smaller than 0.1 μM. The compounds having $IC_{50}$ values smaller than 50 nM are listed in Table 4 together with their $IC_{50}$ values.

TABLE 4

| Compound | $IC_{50}$(nM) |
|---|---|
| 1 | 19.5 |
| 2 | 34.5 |
| 10 | 4.7 |
| 13 | 3.1 |
| 15 | 13.5 |
| 16 | 9.7 |
| 22 | 11.6 |
| 24 | 5.9 |
| 25 | 4.1 |
| 31 | 10.6 |
| 35 | 40.3 |
| 42 | 26.9 |
| 45 | 32.6 |
| 49 | 7.4 |
| 53 | 38.2 |
| 55 | 28.7 |
| 57 | 45.9 |
| 59 | 12.6 |
| 60 | 30.6 |
| 61 | 15.9 |
| 67 | 42.2 |
| 69 | 29.8 |
| 70 | 14.1 |
| 73 | 18.9 |
| 77 | 10.5 |
| 79 | 32.0 |
| 81 | 37.8 |
| 84 | 15.8 |
| 86 | 21.4 |
| 87 | 5.4 |
| 88 | 45.1 |
| 89 | 22.4 |
| 91 | 28.9 |
| 93 | 41.8 |
| 94 | 7.6 |
| 95 | 18.1 |
| 99 | 9.0 |
| 100 | 6.0 |
| 101 | 41.1 |
| 102 | 3.8 |
| 103 | 8.2 |
| 104 | 27.2 |
| 105 | 16.2 |
| 107 | 30.0 |
| 109 | 31.7 |
| 112 | 20.3 |
| 113 | 7.1 |
| 114 | 16.4 |
| 118 | 11.3 |

TEST EXAMPLE 2

Membrane Permeability Experiment

In the development of pharmaceuticals, membrane permeability is an important factor to consider from the viewpoint of relationship with the bodily absorption of a medicament to be administered orally. Compounds having high membrane permeability are expected to feature satisfactory absorption by the intestinal tract (see Pharmaceutical Research (2002) Vol. 19, No. 7, 921-925.)

A membrane permeability test was conducted using PAMPA Evolution™ (pION INC.) in accordance with a modified version of the recommended protocol of pION INC. To be more specific, solutions of an assay compound (i.e., a DMSO solution of the compound as diluted by being added to system solutions that had been adjusted to prescribed pHs (4.0, 5.0, 6.2, and 7.4)) were prepared and added to the lower compartment (donor) of a sandwich plate having a lipid bilayer membrane formed of an artificial lipid (GIT-0). An acceptor sink buffer was added to the upper compartment (acceptor) and after the lapse of a prescribed period, the cumulative permeation of the compound was measured by performing UV spectroscopy on the solutions in the donor and acceptor, and the membrane permeability coefficient Pe ($\times 10^{-6}$ cm/sec) was calculated to assay the membrane permeability of the compound. As it turned out, the subject application compound Nos. 2, 5, 12, 15, 16, 18, 22, 24, 26, 27, 32, 33, 34, 35, 51, 55, 59, 60, 61, 66, 70, 71, 79, 86, 87, 89, 91, 95, 96, 99, 100, 103, 109 and 110 had higher Pe values than the high permeability marker compound metoprolol, thus indicating their satisfactory membrane permeability.

TEST EXAMPLE 3

Test for Recognizability of P-gp Substrate

In order that drugs acting on the central nervous system will develop their efficacy, their passage from the blood to the brain is generally important. While various efflux transporters are present at the blood-brain barrier to control this passage of drugs, P-glylcoprotein (P-gp) is a typical example and inhibits the passage to the brain of any drugs that serve as the substrate for P-gp. Therefore, in the development of pharmaceuticals, nonrecognizability of a candidate drug as the substrate for P-gp is the key to its passage to the brain.

A test for recognizability of P-gp substrate was performed in accordance with a modified version of the methods described in J. Pharmacol. Exp. Ther. (1992) Vol. 263, No. 2, 840-845 and J. Biol. Chem. (1992) Vol. 267, No. 34, 24248-24252. To be more specific, LLC-GA5-COL 300 cells (Human MDR1 expressing system derived from pig kidney derived, cultured renal epithelial cell line LLC-$PK_1$) were cultured for 4 days on a transwell and replaced by a Hank's balanced salt solution (HBSS) in each well just before the test. A solution of an assay compound (a DMSO solution of the compound as diluted with HBSS and adjusted to a final concentration of 10 μM) was added to the donor side of the LLC-GA5-COL 300 cells and a prescribed amount of HBSS was collected from the acceptor side at given time intervals and the concentration of the assay compound in the collected sample was measured by LC-MS/MS.

From the cumulative amount of the compound's permeation into the acceptor, the membrane permeability coefficient ($\times 10^{-6}$ cm/sec) was calculated for each of apical→basal mode and basal→apical mode and the recognizability of P-gp substrate was assessed in terms of the ratio between the two modes (efflux ratio).

As a result, according to the criteria described in Nature Reviews Drug Discovery (2010), Vol. 9, 215-236, the subject application compound Nos. 10 and 49 were found to be not recognizable as the substrate for P-gp, suggesting the possibility of their satisfactory passage to the brain (see Pharmaceutical Research (2001), Vol. 18, No. 12, 1660-1668.) From this result, it is expected that the subject application compounds will be effectively used as drugs that act on the central nervous system.

Industrial Applicability

The invention compounds have a type 1 glycine transporter (GlyT1) inhibiting action and, hence, is effective in the prevention or treatment of diseases associated with the glycine transporter, which specifically include schizophrenia, Alzheimer's disease, cognitive dysfunction, dementia, anxiety disorders (generalized anxiety disorder, panic disorder, obsessive-compulsory disorder, social anxiety disorder, posttraumatic stress disorder, specific phobia, acute stress disorder, etc.), depression, drug addiction, spasm, tremor, sleep disorder and the like.

The invention claimed is:

1. A compound of the formula [I] or a pharmaceutically acceptable salt thereof:

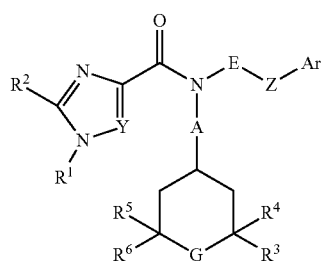

[I]

wherein
$R^1$ represents a hydrogen atom, a $C_{1-6}$ alkyl group, a $C_{3-6}$ cycloalkyl group, a $C_{1-6}$ haloalkyl group, or a $C_{1-6}$ alkoxy $C_{1-6}$ alkyl group;
$R^2$ represents a hydrogen atom, a $C_{1-6}$ alkyl group, a halogen atom, or a $C_{1-6}$ alkoxy group;
or, alternatively, $R^1$ and $R^2$ may, taken together, form a $C_{3-4}$ alkylene group;
Ar represents a phenyl group or a naphthyl group, provided that the phenyl or naphthyl group may be substituted by 1 to 5 substituents selected from among a $C_{1-6}$ alkyl group, a $C_{1-6}$ alkoxy group optionally substituted by a $C_{3-6}$ cycloalkyl group, a $C_{3-6}$ cycloalkoxy group, a $C_{1-6}$ haloalkyl group, a $C_{1-6}$ haloalkoxy group, a halogen atom, a phenyl group (which phenyl group may be substituted by 1 to 5 substituents selected from among a halogen atom, a $C_{1-6}$ alkyl group, a $C_{1-6}$ hydroxyalkyl group, a $C_{1-6}$ cyanoalkyl group, a $C_{1-6}$ alkoxy group, a $C_{2-7}$ alkoxycarbonyl group, a $C_{1-6}$ haloalkyl group, a $C_{1-6}$ haloalkoxy group, and a phenoxy group), a phenoxy group that may be substituted by 1 to 5 halogen atoms, a pyridyl group, an imidazolyl group, a pyrazolyl group, and a cyano group;
Y represents a nitrogen atom or the formula CH;
Z represents a single bond or an oxygen atom;
A represents a single bond or a $C_{1-3}$ alkylene group;
E represents a $C_{1-3}$ alkylene group that may be substituted by a $C_{2-7}$ alkoxycarbonyl group, a phenyl group or a $C_{1-6}$ hydroxyalkyl group;
G represents an oxygen atom, a sulfur atom, or the formula $SO_2$;
$R^3$, $R^4$, $R^5$, and $R^6$, which may be the same or different, represent a hydrogen atom or a $C_{1-6}$ alkyl group.

2. The compound according to claim 1, wherein G is an oxygen atom, or a pharmaceutically acceptable salt thereof.

3. The compound according to claim 1, wherein Ar is a phenyl group substituted by 1 to 5 substituents selected from among a $C_{1-6}$ haloalkyl group, a $C_{1-6}$ haloalkoxy group, a halogen atom, a $C_{1-6}$ alkyl group, and a phenyl group (which phenyl group may be substituted by 1 to 5 substituents selected from among a halogen atom, a $C_{1-6}$ hydroxyalkyl group, a $C_{1-6}$ alkoxy group, a $C_{2-7}$ alkoxycarbonyl group, a $C_{1-6}$ haloalkyl group, a $C_{1-6}$ haloalkoxy group, a $C_{1-6}$ alkyl group, a $C_{1-6}$ cyanoalkyl group, and a phenoxy group), or a pharmaceutically acceptable salt thereof.

4. The compound according to claim 1, wherein Ar is a phenyl group or a naphthyl group, provided that the phenyl or naphthyl group may be substituted by 1 to 5 substituents selected from among a $C_{1-6}$ alkyl group, a $C_{1-6}$ alkoxy group, a $C_{1-6}$ haloalkyl group, a $C_{1-6}$ haloalkoxy group, a halogen atom, a phenyl group which may be substituted by 1 to 5 halogen atoms, a phenoxy group that may be substituted by 1 to 5 halogen atoms, a pyridyl group, an imidazolyl group, a pyrazolyl group, and a cyano group; E is a $C_{1-3}$ alkylene group; G is an oxygen atom; $R^3$, $R^4$, $R^5$, and $R^6$ are each a hydrogen atom, or a pharmaceutically acceptable salt thereof.

5. The compound according to claim 1, wherein $R^1$ is a $C_{1-6}$ alkyl group, $R^2$ is a hydrogen atom, and Y is a nitrogen atom, or a pharmaceutically acceptable salt thereof.

6. The compound according to claim 1, wherein $R^1$ is a hydrogen atom or a $C_{1-6}$ alkyl group, $R^2$ is a hydrogen atom, and Y is the formula CH, or a pharmaceutically acceptable salt thereof.

7. The compound according to claim 1, wherein Z and A are each a single bond, and E is a methylene group, or a pharmaceutically acceptable salt thereof.

8. The compound according to claim 1, wherein Ar is a phenyl group substituted by 1 to 5 substituents selected from among a $C_{1-6}$ haloalkyl group, a $C_{1-6}$ haloalkoxy group, and a halogen atom, or a pharmaceutically acceptable salt thereof.

9. A pharmaceutical composition comprising as an active ingredient the compound according to claim 1 or a pharmaceutically acceptable salt thereof, and a pharmacologically acceptable carrier.

* * * * *